United States Patent [19]
Brownlee

[11] Patent Number: 5,772,693
[45] Date of Patent: Jun. 30, 1998

[54] SINGLE PREFORMED CATHETER CONFIGURATION FOR A DUAL-CHAMBER PACEMAKER SYSTEM

[75] Inventor: Robert R. Brownlee, Ormond Beach, Fla.

[73] Assignee: Cardiac Control Systems, Inc., Palm Coast, Fla.

[21] Appl. No.: 625,067

[22] Filed: Mar. 29, 1996

Related U.S. Application Data

[63] Continuation-in-part of Ser. No. 598,992, Feb. 9, 1996, abandoned.

[51] Int. Cl.⁶ ............................................. A61N 1/05
[52] U.S. Cl. ............................. 607/123; 607/126
[58] Field of Search ........................ 607/119, 122, 607/123, 125, 126, 127

[56] References Cited

U.S. PATENT DOCUMENTS

| | | | |
|---|---|---|---|
| 4,010,755 | 3/1977 | Preston | 128/404 |
| 4,154,247 | 5/1979 | O'Neill | 128/419 P |
| 4,217,913 | 8/1980 | Dutcher | 128/785 |
| 4,374,527 | 2/1983 | Iversen | 128/785 |
| 4,394,866 | 7/1983 | Hughes | 128/785 |
| 4,401,126 | 8/1983 | Reenstierna | 178/784 |
| 4,402,322 | 9/1983 | Duggan | 607/9 |
| 4,414,986 | 11/1983 | Dickhudt et al. | 128/785 |
| 4,422,460 | 12/1983 | Pohndorf | 128/786 |
| 4,627,439 | 12/1986 | Harris | 128/419 P |
| 5,127,403 | 7/1992 | Brownlee | 128/419 P |
| 5,133,365 | 7/1992 | Heil, Jr. et al. | 128/786 |
| 5,265,602 | 11/1993 | Anderson et al. | 607/122 |
| 5,387,233 | 2/1995 | Alferness et al. | 607/126 |
| 5,628,778 | 5/1997 | Kruse et al. | 607/125 |

FOREIGN PATENT DOCUMENTS

| | | | |
|---|---|---|---|
| 0453589 | 10/1990 | European Pat. Off. | 607/9 |

*Primary Examiner*—William E. Kamm
*Attorney, Agent, or Firm*—Kerkam, Stowell, Kondracki & Clarke; Dennis P. Clarke

[57] ABSTRACT

A single preformed catheter configuration for a dual-chamber pacemaker system is provided. The catheter is formed of a heat-settable biocompatible material such as, for example, polyether polyurethane, and is formed in a predetermined shape to enhance and stabilize atrial electrode contact on the inner wall of the atrium, while also providing stress relief to absorb stresses occasioned by cardiac depolarization and respiration and modulation of the bulk cardiac complex. To this end, the catheter of the present invention includes a first section disposed in the superior vena cava to provide substantially stable support to the catheter, a second section disposed in the atrium and being preformed to substantially conform to the inner wall of the atrium, and a third section having a pliancy greater than that of the first two sections and being disposed distally of the second section. The first section disposed in the superior vena cava may have one of a variety of geometries, including, but not limited to, a plurality of curves, a spiral or helical configuration and a single reverse bend or lobe.

55 Claims, 18 Drawing Sheets

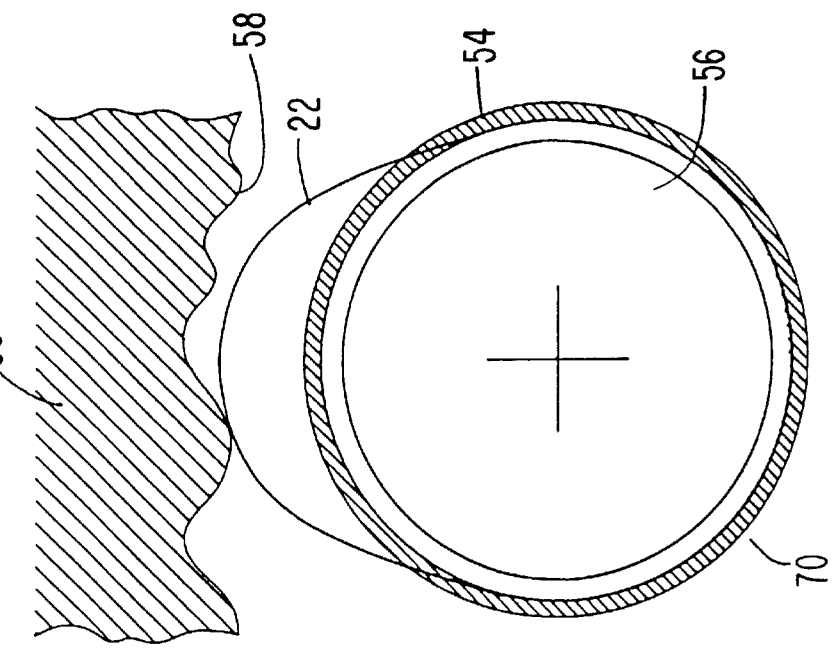
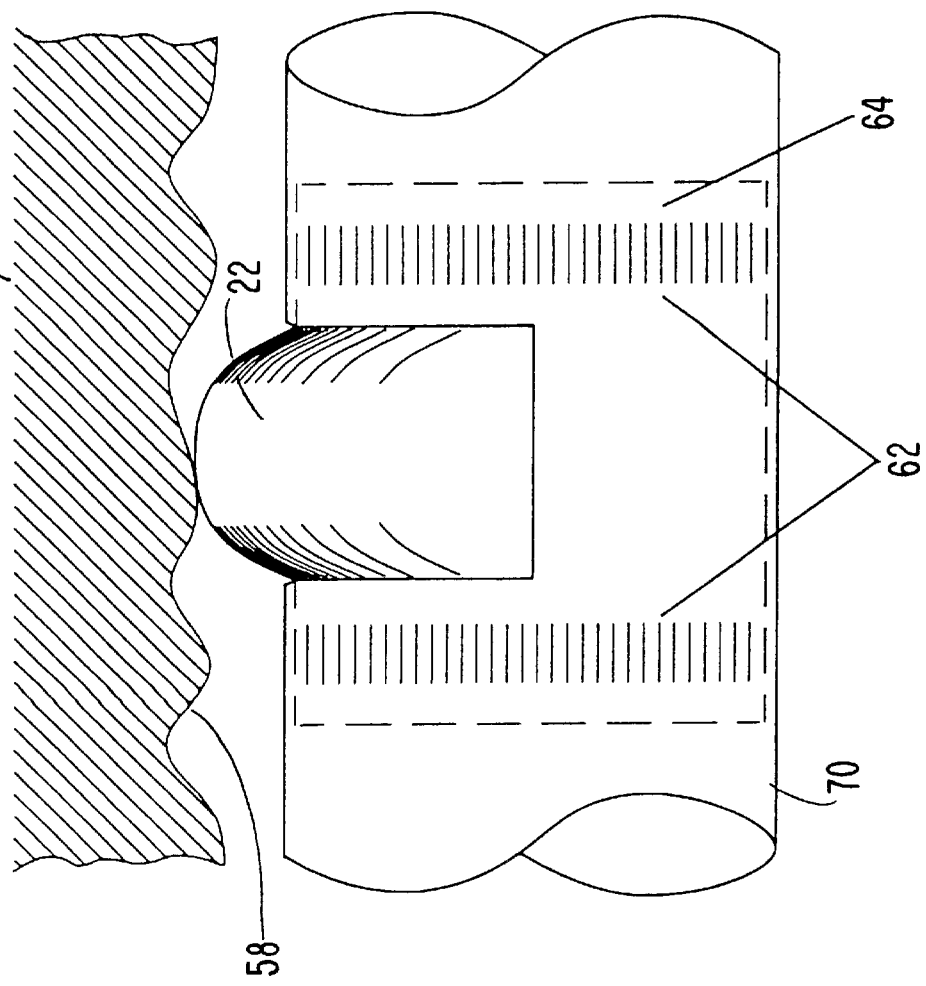

SINGLE PREFORMED CATHETER CONFIGURATION FOR A DUAL-CHAMBER PACEMAKER SYSTEM

CROSS-REFERENCE TO RELATED APPLICATION

The present application is a continuation-in-part of the present inventor's co-pending U.S. application Ser. No. 08/598,992 filed Feb. 9, 1996, hereby incorporated by reference, and abandoned following the filing of the present application.

BACKGROUND OF THE INVENTION

1. Field of the Invention

The present invention relates to a catheter configuration for a dual-chamber pacemaker system. In particular, the configuration employs a heat-settable polyurethane catheter having a plurality of electrodes, wherein the catheter is formed to provide stable support to the atrial electrodes and ensure proper contact of the atrial electrodes on the inner wall of the atrium, while also providing stress relief to absorb stresses on the configuration occasioned by respiration and contraction of the bulk cardiac complex.

2. Discussion of the Prior Art

There are numerous catheter configurations disclosed in the prior art that purport to provide a solution to the application of a single catheter for dual-chamber pacing. These prior art systems use a variety of methods and configurations in an attempt to provide stable contact of electrodes with cardiac tissue, especially in the atrial chamber of the heart. However, prior art configurations have had limited commercial success and have not satisfactorily provided a solution that would enable single-catheter, dual-chamber pacing. Some of the problems encountered include difficulty of catheter placement, use of inadequate stabilization mechanisms and poor atrial pacing and sensing functionality. The failure to provide an acceptable solution has prompted physicians to continue using systems employing two separate catheter leads in spite of the high complication rate inherent in these systems.

An example of a single-catheter solution is shown in U.S. Pat. No. 4,401,126 to Reenstierna, which discloses a large preformed circular loop that is said to provide a catheter shape that provides conformance of the catheter to the atrial wall and stability of position along the atrial wall (see FIG. 1). However, the looped catheter configuration of Reenstierna, which is purportedly shaped to enhance maintenance of electrode contact with atrial tissue, is mechanically inappropriate to serve its intended function. Specifically, in Reenstierna's configuration, the loop employed to fix or stabilize the position of the curved portion of the catheter housed along the atrial wall terminates in an essentially free-floating position in the horizontal plane where the catheter exits the superior vena cava. This placement of the loop allows horizontal free motion of the catheter, which does not provide adequate holding forces to serve as a stabilizing means for the catheter section disposed along the atrial wall. Reenstierna further asserts that the looped coil serves as a member for absorbing movement of the heart, thereby insulating the portion of the catheter along the wall of the atrium from movements that would otherwise displace the electrodes. However, upon closer examination, it is readily apparent that this is not the case. In particular, the major motional forces on the catheter of Reenstierna are induced in the distal ventricular end of the catheter during ventricular depolarization. The loop portion of the catheter, which allegedly absorbs the heart movement, is disposed above the atrial wall portion of the catheter. Because the movement is induced in the ventricle, the loop disposed above the atrial portion of the catheter cannot absorb this ventricular-induced motion without disruption of the atrial wall section of the catheter. It must also be recognized that Reenstierna's configuration does relieve longitudinal motion and deformation stresses induced by respiration at the superior vena cava site. However, it is clear that Reenstierna's configuration does not adequately reduce ventricular-induced stresses. Reenstierna further expresses the potential need to strengthen only the section of the catheter disposed along the atrial wall, but fails to recognize that in order to provide adequate counter forces that oppose the forces applied to the catheter along the atrial wall, the loop stabilization means being strengthened only in the section of the catheter along the atrial wall would be inappropriate and ineffective.

U.S. Pat. No. 4,374,527, to Iversen discloses a body-stimulation lead having multiple lobes formed therein for absorbing body forces by deforming longitudinally in compression and elongation to minimize the influence of forces on electrodes positioned on other sections of the catheter. The configuration taught by Iversen is only useful in mitigating longitudinal forces and is not effective for holding purposes in the shaped region and for reducing horizontal forces, such as those induced by respiration. There is no means provided in Iversen to hold the catheter in place, especially in a position within the atrial chamber of the heart.

In U.S. Pat. No. 4,414,986, to Dickhudt et al., a catheter for use in spinal cord stimulation is disclosed. Spiral loops are formed in the catheter to relieve longitudinal stresses placed on the catheter when it is disposed in the epidural space. The loop configuration of Dickhudt et al. is designed to resist movement of the catheter in a direction parallel to the axis of the lead. In a spinal application, this would be in the up-and-down direction. However, no configuration is provided to mitigate horizontal, or other, forces induced on the lead which are remote from the body cavity in which the lead is disposed.

U.S. Pat. No. 4,394,866, to Hughes, discloses a helical lead for atrial leads only. The spiral loops of the catheter are disposed in the superior vena cava and purportedly provide stabilization of atrial electrodes only. There is no structural element which would provide mitigation of remotely induced movement, i.e., movement of the electrodes due to ventricular forces on a ventricular lead.

None of the prior art systems discussed provides a single-catheter, dual-chamber pacing and sensing system that includes stress relief mechanisms that cooperate with stabilization mechanisms to ensure proper electrode contact with the desired areas within a specific chamber of the heart, while maintaining the desired contact in spite of movements and stresses on the catheter occasioned by remote and cardiac bulk complex movements.

SUMMARY OF THE INVENTION

The present invention provides an improved apparatus that overcomes the deficiencies of known single-catheter systems with respect to providing proper electrode contact while mitigating the effects of stresses placed on the catheter by both locally and remotely induced motional forces on the catheter. In particular, the present invention uses a single preformed catheter which is formed to provide cantilevered support and stabilization by providing distributed pressure stabilizing contact points in the superior vena cava, preformed atrial wall conformity to assure atrial electrode contact and increased pliancy of the catheter distal to the atrial electrodes, thereby providing stress relief above and below the tricuspid valve to mitigate motion of the atrial electrodes and ventricular electrode during the cardiac and respiratory cycle, while positioning the atrial and ventricular electrodes to optimize pacing and sensing.

Accordingly, it is an object of the present invention to provide a single-catheter, dual-chamber pacemaker system wherein the catheter is preformed to provide stress relief and motional stability to the catheter and electrode arrangement.

It is another object of the present invention to place electrodes in positions that ensure optimal sensing and pacing of the atrial and ventricular chambers of the heart.

A further object of the present invention is to reduce the effect of external forces on the atrial electrodes using the catheter configuration to mitigate the forces.

It is yet another object of the present invention to provide improved pacing and sensing of the heart using a single-catheter configuration.

An additional object of the present invention is to stabilize the position of the atrial electrodes using catheter configurations that are supported by their position and shape within the superior vena cava.

A still further object of the present invention is to provide improved pacing and sensing using electrodes that face only the wall of the atrium in which they are disposed.

Another object of the present invention is to isolate the atrial electrodes from ventricularly induced motion by providing a catheter having greater pliancy in a portion that is distal of the atrial electrodes and that extends through the tricuspid valve.

These and other objects, and their attendant advantages, are achieved by the present invention, which provides a single catheter for pacing and sensing both the atrial and ventricular chambers of the heart, comprising: preformed stabilization configuration of the catheter disposed primarily in the superior vena cava; atrial electrodes disposed on an atrial section of the catheter and being arranged to conform to the atrial wall and being held in proximity to the atrial wall by the stabilization configuration of the catheter disposed primarily in the superior vena cava; a stress relief portion of the catheter disposed between the atrial electrodes and the distal end of the catheter termination in the ventricular chamber of the heart; and a ventricular electrode disposed at the distal end of the catheter for pacing and sensing the ventricular chamber of the heart.

BRIEF DESCRIPTION OF THE DRAWINGS

The invention will be described in detail herein with reference to the following drawings in which like reference numerals refer to like elements throughout the several views, and wherein:

FIG. 11 is an elevational schematic view of a preferred electrode configuration of the present invention;

FIG. 12 is a cross-sectional view of the electrode configuration shown in FIG. 11;

DETAILED DESCRIPTION OF THE PREFERRED EMBODIMENTS

Figure 1:
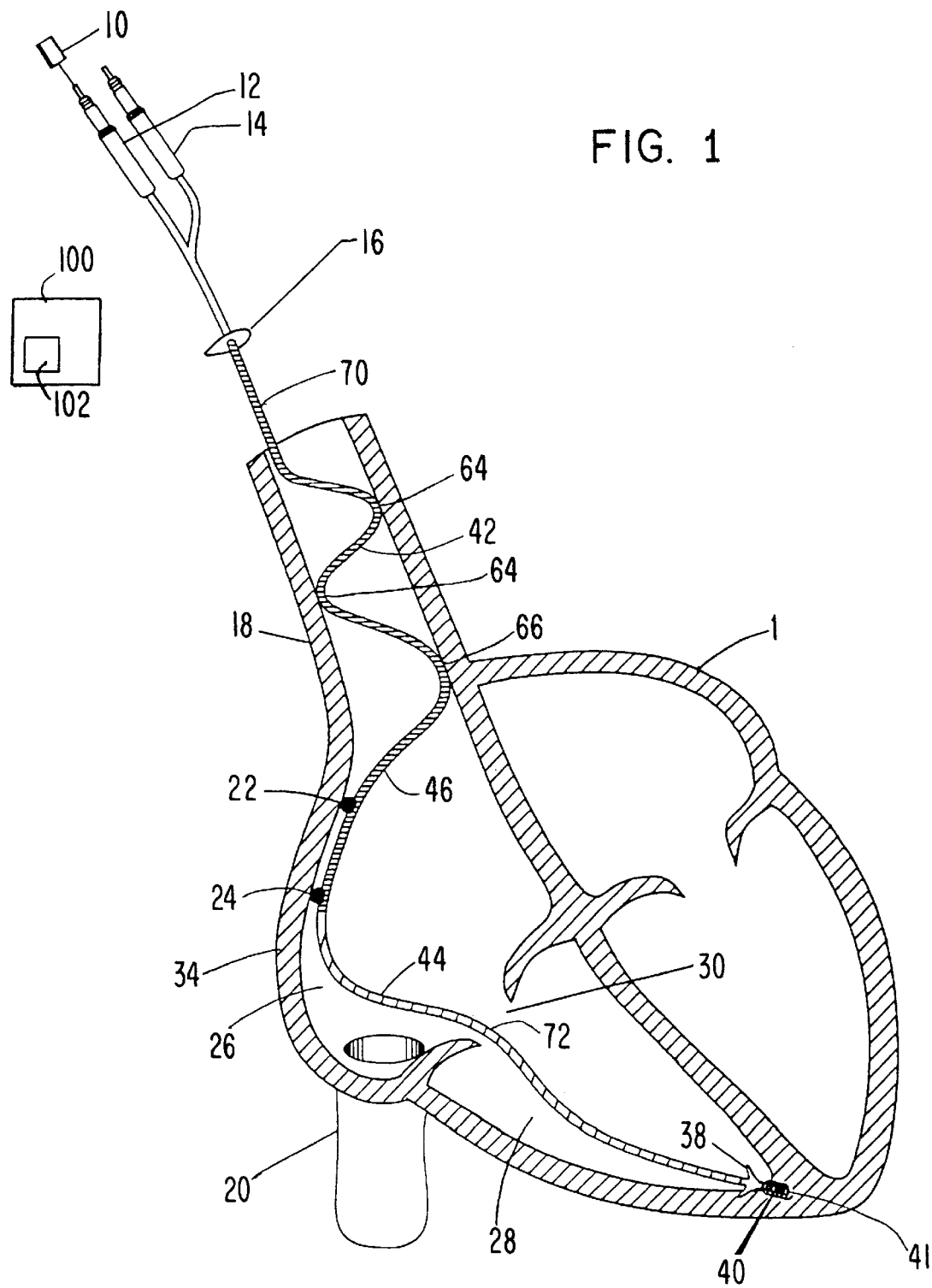
FIG. 1 is a schematic cross-sectional view of an embodiment of the present invention in which stabilization configuration is a plurality of curved portions.

FIG. 1 is a cross-sectional view of one embodiment of the present invention employing a plurality of curved portions of a catheter in the superior vena cava. The catheter 70 is positioned in the heart 1 by passing the catheter 70 through the superior vena cava 18. Implant of the catheter 70 in the heart 1 is normally accomplished using known techniques, such as, for example, using a stylet 10 to straighten the preformed catheter 70 for insertion via the superior vena cava 18. Once insertion has been satisfactorily accomplished, the stylet 10 is removed from the catheter 70 and the catheter 70 assumes the preformed shape according to any of the exemplary embodiments described herein. The catheter 70 includes connectors 12, 14 for providing electrical connection between the electrodes 22, 24 and an implanted medical device such as, for example, a pacemaker 100. The catheter 70 may also optionally include a tie-down stabilizer and position indicator 16 which is useful in positioning the catheter 70 during implant and stabilizing catheter position post-implant. The catheter 70 also includes tines 38 and/or an active fixation screw 40 at a distal end thereof to provide additional stability to the implanted catheter and to ensure proper positioning of a ventricular electrode 41.

The catheter 70 is made of biocompatible insulative materials that are heat-settable to a desired configuration and provide stable memory, i.e., they return to the preformed shape once they have been implanted and after the stylet 10 has been removed. An example of such biocompatible heat-settable material is polyether polyurethane, available from Polymer Technology Corporation under the name BioSpan. Details of the catheter configuration will be discussed below with respect to FIG. 10. The catheter 70 of the present invention facilitates permanent pacing and sensing in two chambers of the heart, such as, for example, the right atrium 26 and the right ventricle 28. It will, of course, be understood that the principles of catheter formation and placement discussed herein with respect to the present invention may be equally applicable to unipolar, bipolar and multiple catheter configurations that are disposed in any selected chambers of the heart, as required.

In the embodiment shown in FIG. 1, multiple curved portions 64, 66 of the catheter 70 are disposed in the superior vena cava 18, and are preformed to provide distributed pressure stabilizing contact points along the inner walls of the superior vena cava 18, where the curved portions press outwardly against the superior vena cava 18. The last curved portion 66, in conjunction with the other curved portions 64, is formed to provide cantilevered support to a portion 46 of the catheter 70 wherein the electrodes 22, 24 are disposed. Additionally, the preformed shape of the catheter 70 in the portion 46 is formed to provide conformity to the atrial wall 34, thereby assuring atrial electrode contact. The catheter 70 is also provided with a relatively pliant portion 44 which extends from an area distal of the electrodes 22, 24 but proximal the tricuspid valve 30. Forming the portion 44 in a manner such that it is more flexible or pliant than the rest of the catheter 70 provides stress relief above and below the tricuspid valve 30 and mitigates motion of the atrial electrodes 22, 24 and ventricular electrode 41 during the cardiac cycle and respiratory cycle. Thus, the catheter 70 should have the same general pliancy down through the location of the electrodes 22 and 24, and have a relatively greater pliancy in the portion 44 below the electrodes 22 and 24.

Figure 2:
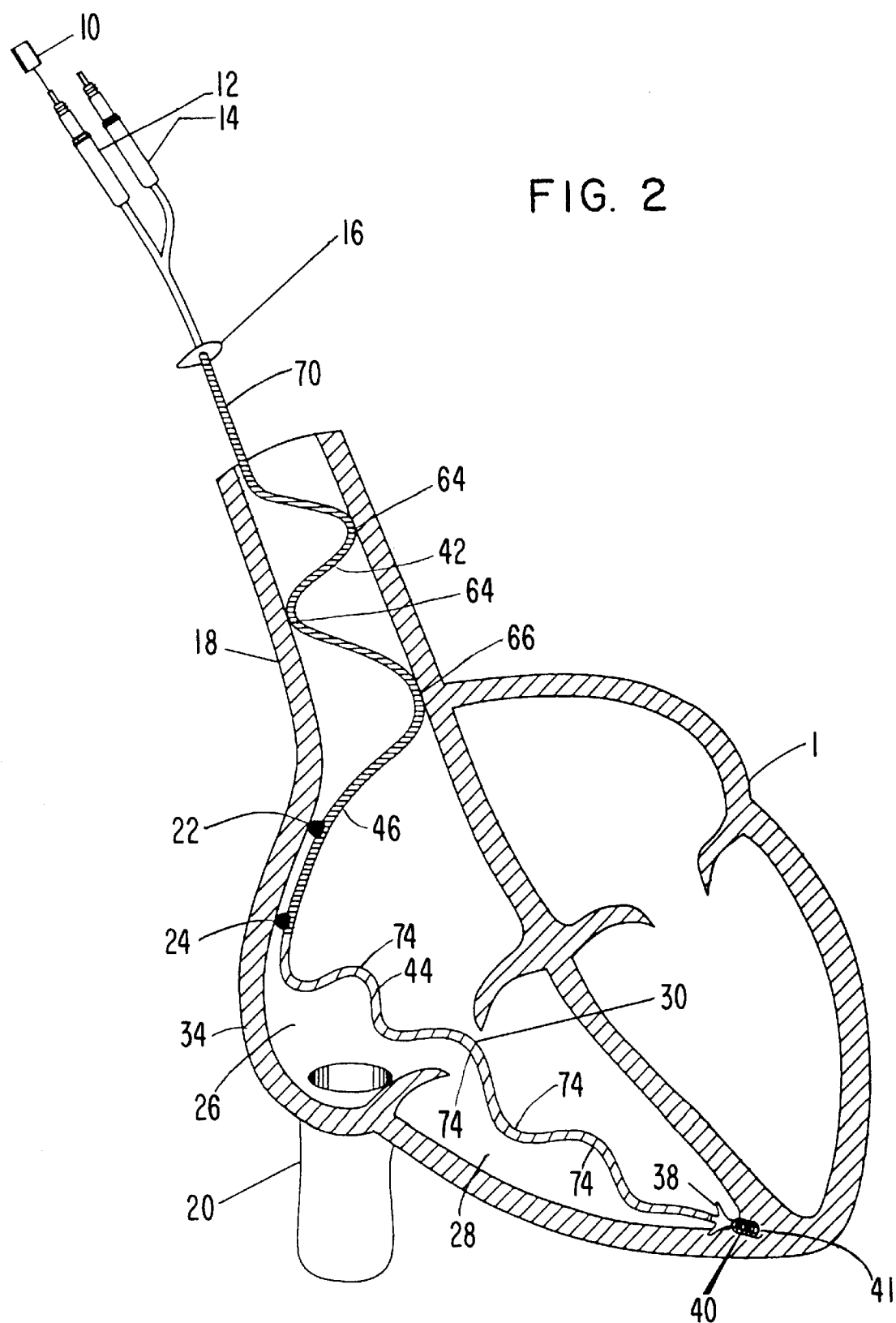
FIG. 2 is a schematic cross-sectional view as shown in FIG. 1, wherein the portion of the catheter between the atrial and ventricular electrodes is also provided with a predetermined amount of additional length and curves.

It is also important to note that optimal atrial electrode placement for optimizing pacing and sensing is achieved by disposing the atrial electrodes 22, 24 principally toward the atrial wall 34. Maintaining this electrode position is, therefore, also an important object. The embodiments shown in FIGS. 1 and 2 depict atrial lateral wall placement of the atrial electrodes 22, 24. Anterior wall placement of the atrial electrodes 22, 24 is also facilitated, if required, as shown in FIG. 3.

Figure 3:
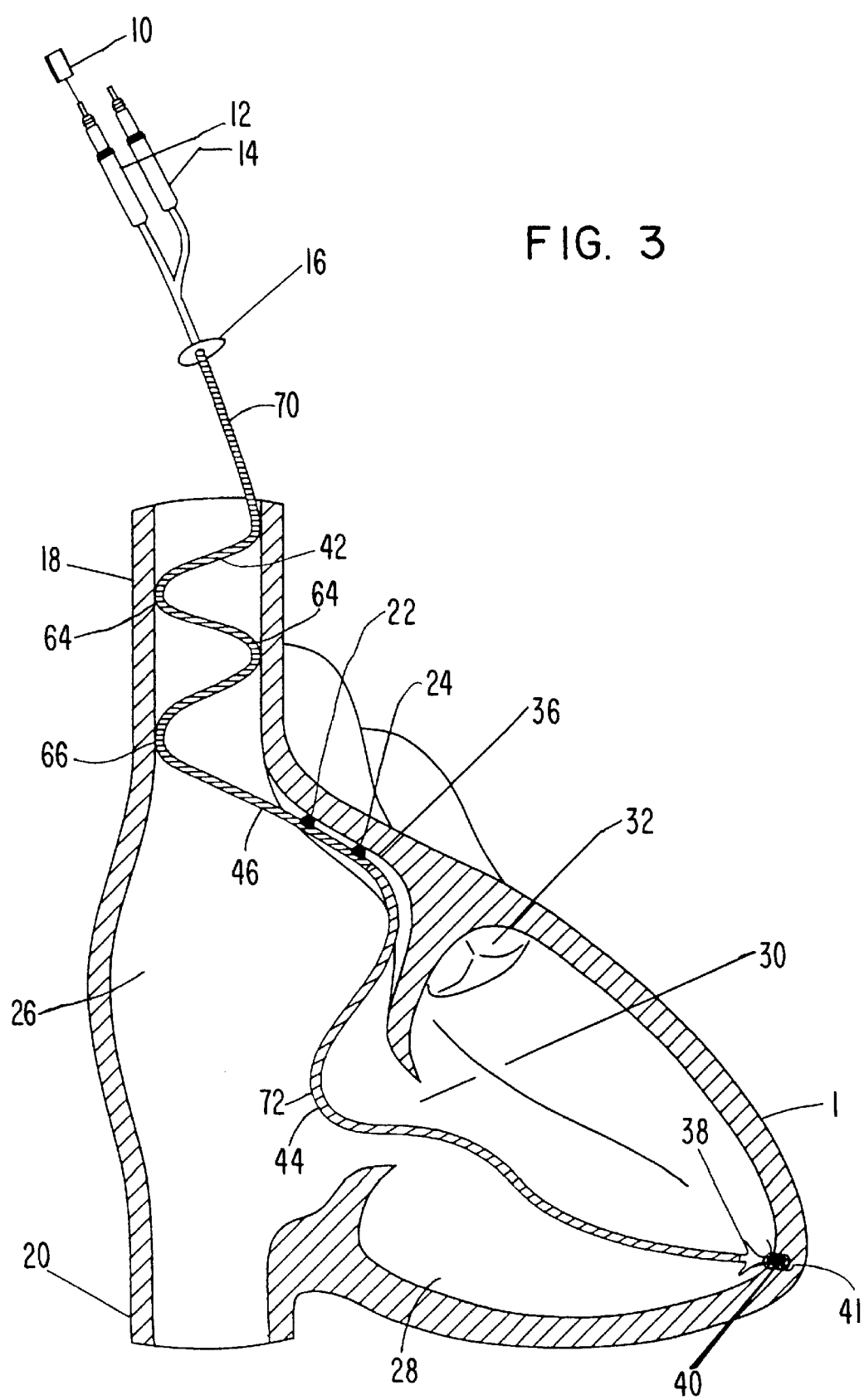
FIG. 3 is a schematic cross-sectional view as shown in FIGS. 1 and 2, but with the atrial electrodes being disposed on the anterior wall of the atrium.

With reference to FIGS. 1–3, the catheter's 70 superior vena cava contact points 64, 66 provide a cantilevered base to stabilize the atrial conformal section of the catheter 70 along the lateral atrial wall 34 or anterior atrial wall 36, as required. Providing a relatively rigid cantilevered base allows the use of a stress-relief shape and a portion of greater pliancy 44 of the catheter 70 below the atrial electrodes 22, 24 and in the ventricular section of the lead as cooperative aids to achieve atrial electrode stability. In other words, the atrial section 46 of the catheter 70 is held in place from above the superior vena cava 18 and isolated from the dominant ventricular motion of the heart 1 by the more flexible and pliant portion 44 of the catheter 70 below the atrial electrodes 22, 24. In contrast to the prior art catheters that use curved portions merely as spring-like shock absorbers to provide elongation and compression of the catheter 70 to relieve longitudinal stresses, the curved portions 64, 66 of the catheter 70 of the present invention provide cantilevered support as a stabilization and holding mechanism to ensure the maintenance of optimal electrode positioning.

Using the combined cantilevered support of the catheter 70 in an area 46 above and including the atrial electrodes 22, 24 and a section below the atrial electrodes 44 having greater pliancy and flexibility allows for mitigation of both respiratory and other body motions and the motions associated with cardiac rhythms. Respiratory motion induced from the diaphragm (not shown), places longitudinal forces on the bulk cardiac complex. This respiratory-induced motion tends to slightly elongate the cardiac structure during inspiration and shorten the cardiac structure during expiration. Diaphragmatic motion also induces motion of the bulk cardiac complex relative to the chest cavity which places stretching forces at the site of the catheter 70 in the superior vena cava 18. Additionally, during contraction of the atrium 26, forces are applied to the superior vena cava 18 conduit that tend to narrow its diameter for valving against backflow of blood during atrial contraction. Both of these deformation forces on the catheter section in the superior vena cava 18 must be absorbed by the catheter 70 structure.

According to the present invention, the major longitudinal forces that modulate the dimensions of the bulk cardiac complex are absorbed in the catheter section 44 below the atrial electrodes 22, 24. Dimensional modulation of the atrial chamber 26 from respiratory motion is absorbed in the arm of the cantilevered section 46 subtending the atrial wall 34 and the wall of the superior vena cava 18. It is also important to note that the atrial electrodes 22, 24 only need to provide contact or very close contact to the atrial wall 34 during the diastolic period or resting state of the entire cardiac complex. The diastolic period is a "settle-down" time in which the catheter 70 has time to reconform to the end diastolic shape of the atrial wall 34 and be in a position to be ready to stimulate the atrium 26 via signals from the pacemaker if the SA nodal rate is below the pacemaker escape rate. Accordingly, if a stimulus is required, the heart 1 has reached its most relaxed state, and the atrial electrodes 22, 24 have had time for repositioning and stabilization against atrial cardiac tissue if they have been displaced during the preceding cardiac systole. If, on the other hand, the SA node provides the excitation to initiate systole of the atrium 26 rather than requiring an artificial pacing stimulus, the resulting atrial wall 34 contraction would be directed toward the atrial electrodes 22, 24 and enhance contact for sensing of the atrial depolarization signal, which, in turn, provides synchronization of the ventricular stimulus delivered from the pacemaker. Even if the atrial electrodes were temporarily displaced from the atrial wall 34 during systole, contact with atrial tissue is not required for sensing atrial depolarization. Accordingly, the present invention provides a unipolar catheter configuration wherein atrial electrode contact for atrial stimulation is stabilized at the end diastolic period when it is needed, and if not needed, SA excitation of the atrium 26 will cause atrial wall 34 motion most likely in a direction to assist atrial sensing. If electrode contact is lost during atrial systole, sensing may still be accomplished from the electrodes 22, 24 in a blood pool location.

The catheter configuration depicted in FIG. 2 is the same as that shown in FIG. 1, but providing a pliant section 44 that has additional length to facilitate greater absorption of cardiac-induced motions. The catheter configuration shown in FIG. 3 is one in which the atrial electrodes 22, 24 are positioned to be along the anterior wall 36 of the atrium 26. It is noted that the pliant section 44 of the configuration shown in FIG. 3 may be provided with additional length as shown in FIG. 2. The length of the pliant section 44, required in a particular application, is determinable by one of ordinary skill.

Figure 4:
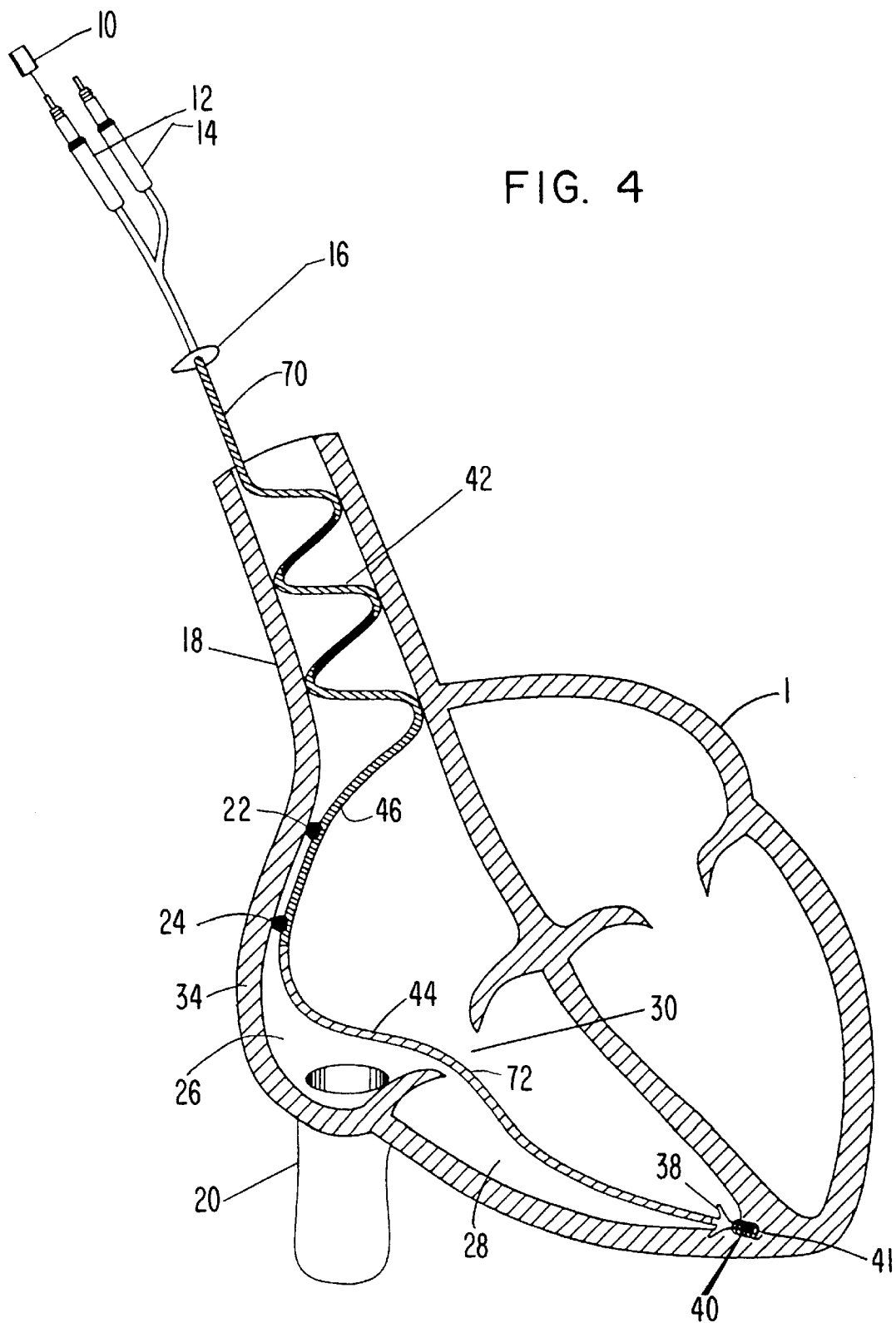
FIG. 4 is a schematic cross-sectional view of the present invention wherein the stabilization configuration is in the form of a spiral section disposed in the superior vena cava.
Figure 5:
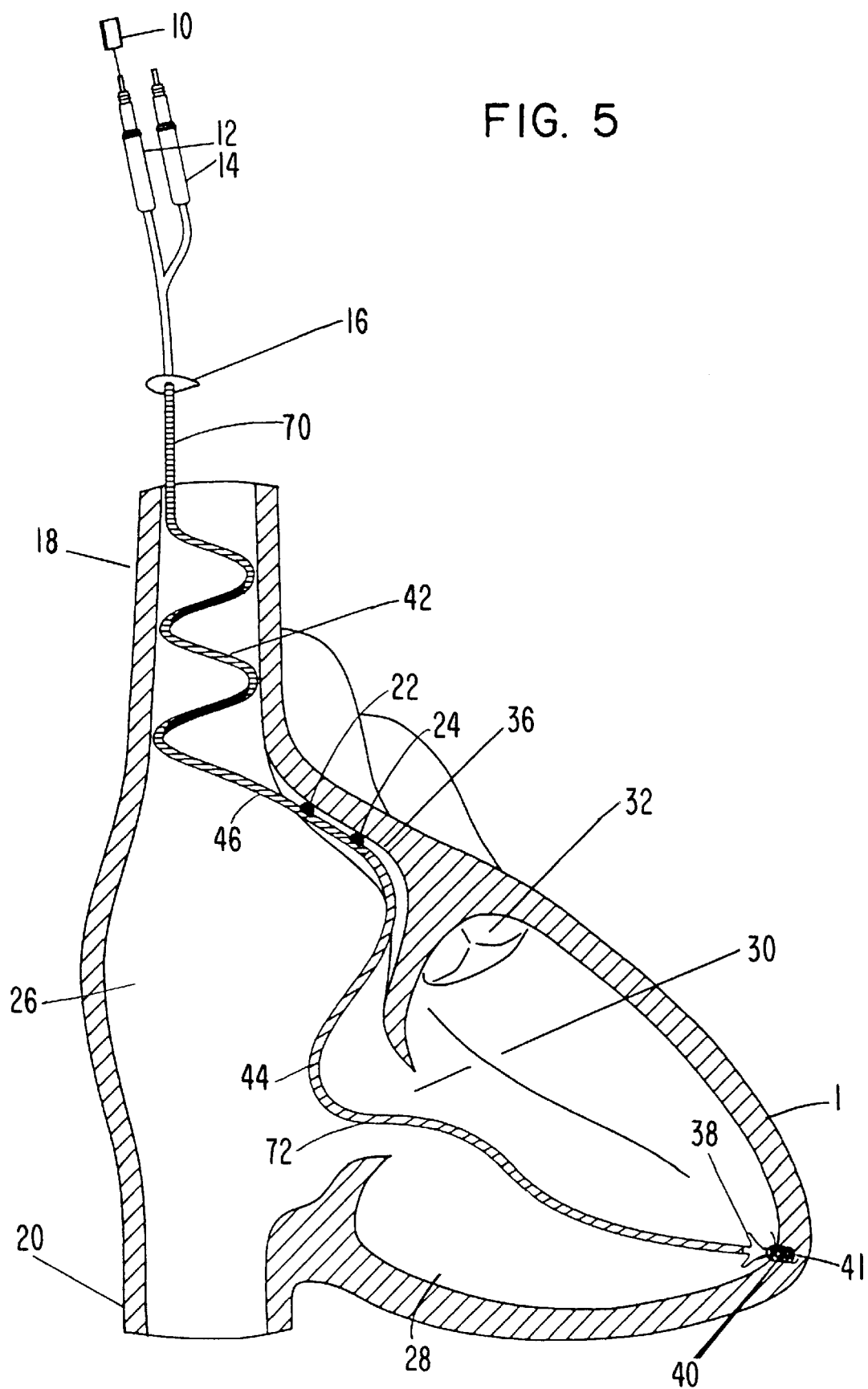
FIG. 5 is a schematic cross-sectional view of the embodiment of the present invention shown in FIG. 4, but with the atrial electrodes being disposed on the anterior wall of the atrium.

Turning now to FIGS. 4 and 5, the catheters depicted in these figures are similar to those depicted in FIGS. 1–3, with the exception that the "holding" portion 42 of the catheter 70 contained within the superior vena cava 18 is of a generally helical or spiral shape. In this embodiment, the cantilevered support structure employs a substantially spiral shape in the superior vena cava 18 to provide stability of the conformal atrial section 46 of the catheter 70. According to the present invention, the spiral configuration portion 42 of the catheter 70 disposed in the superior vena cava 18 is used only for holding purposes and for direct deformation with and during deformation of the superior vena cava 18. Stress relief from ventricular motion is provided by the more pliant section 44 of the catheter 70 disposed distally and past the atrial electrodes 22, 24 as described above with respect to FIGS. 1–3. In other words, the stabilization function and the stress-release function are employed as distinctly separate mechanisms with one mechanism disposed proximal to the atrial electrodes 22, 24 and the other distal to the atrial electrodes 22, 24. FIG. 5 is similar to FIG. 3 in that it positions the atrial electrodes 22, 24 along the anterior atrial wall 36 of the atrium 26. However, the configuration shown in FIG. 5 uses a spiral holding configuration in the superior vena cava 18 as shown in FIG. 4.

Figure 6:
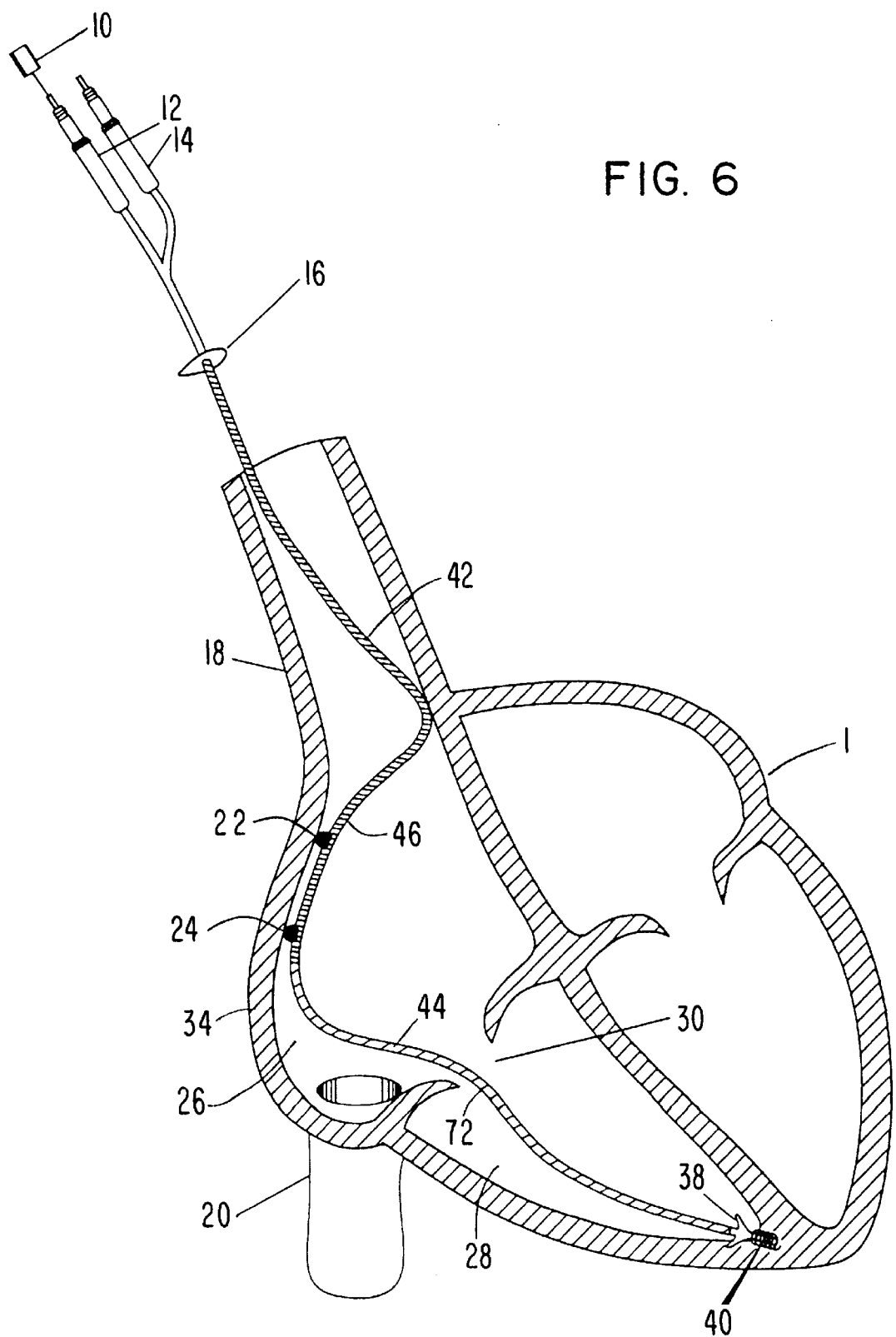
FIG. 6 is a schematic cross-sectional view of the present invention wherein the stabilization configuration is a substantially "U"-shaped, or lobed, portion of the catheter disposed in the superior vena cava.

In another embodiment of the present invention, as illustrated in FIG. 6, the superior vena cava region 42 of the catheter 70 relies on a preformed "U"-shape, or lobe, having large enough dimensions to apply holding forces at one location in the superior vena cava 18 exit area, while providing opposing forces at the section 46 containing the atrial electrodes 22, 24 disposed against the atrial wall 34. In this embodiment, a single reverse bend is employed at the superior vena cava exit to provide a fulcrum for lever action against the section of the catheter proximal to the curved portion that traverses and contacts the opposite wall of the superior vena cava 18. This configuration also employs control of the pliancy and stress relief bends below the atrial section 46 of the catheter 70 as described above with respect to FIGS. 1–5. It is also noted that the single curved configuration shown in FIG. 6 is equally applicable to applications which require atrial electrode placement along the anterior wall of the atrium.

Figure 7:
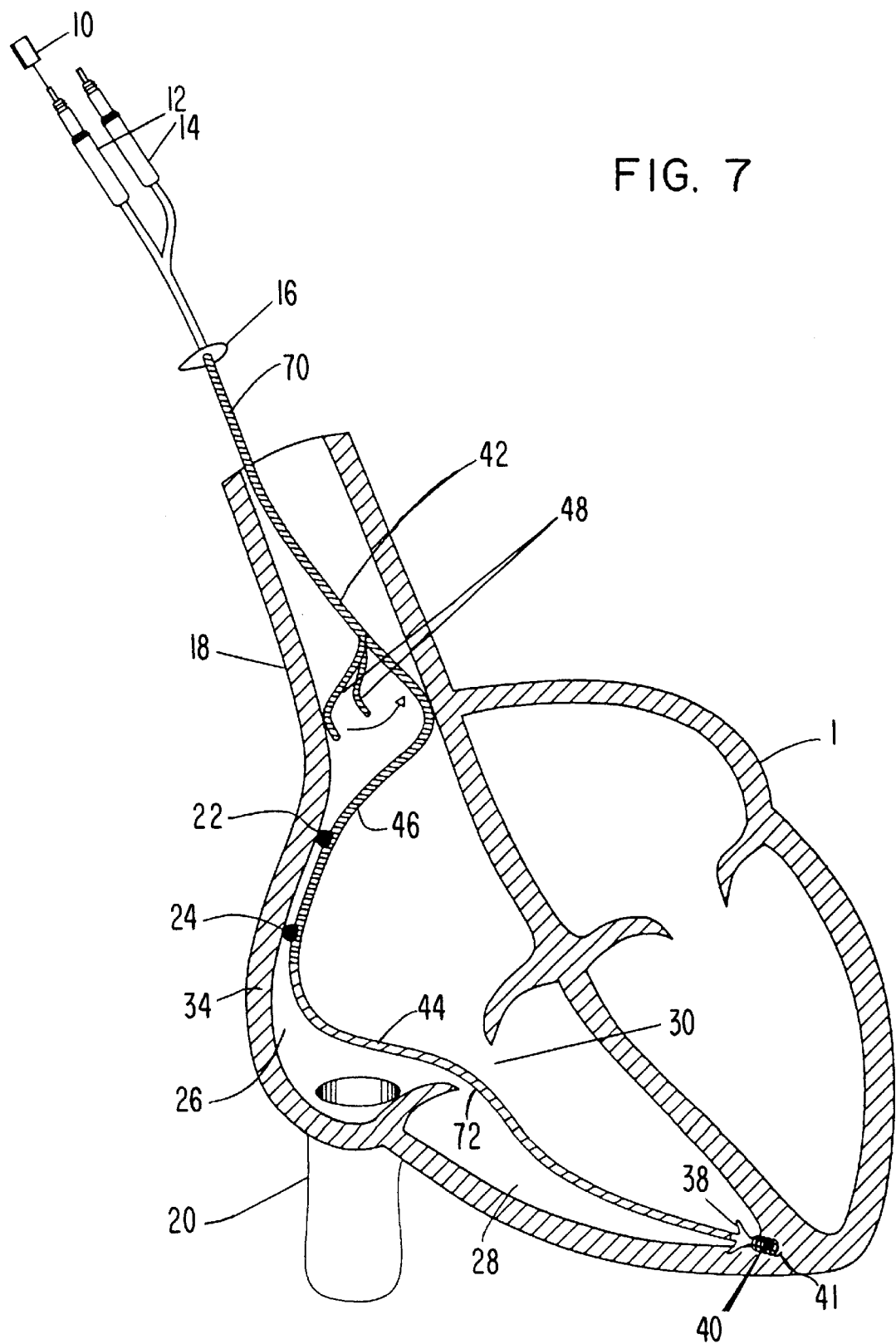
FIG. 7 is a schematic cross-sectional view of the present invention wherein the stabilization configuration includes splayed projections disposed in the superior vena cava.

FIG. 7 shows another embodiment of the present invention in which two preformed arms 48 are shown splayed away and angularly positioned, preferably at angles of 120° from the main catheter body. Each arm is also preferably separated from the other by an angle of 120°. The arms 48 in combination with the preformed catheter 70 provide a balanced three-point stabilizing mechanism for the base of the cantilevered section 46 of the catheter 70 disposed along the atrial wall 34. It will be understood that means for compressing the arms 48 next to the catheter body 70 during insertion into the venous system will be required and that preforming the arms 48 using the same materials as used to house the catheter body 70 will provide sufficient spring-loading so that the arms 48 can perform their desired function. Examples of such compression means include, for example, a tie strand that can be pull-released at the proximal connector 12 end of the catheter following insertion of the catheter 70, a biocompatible dissolvable restraint that releases the splayed projections 48 upon sustained contact with blood, or simple manual deformation of the projections 48 for insertion via a catheter introducer. It will also be understood that the splayed arm configuration shown in FIG. 7 is equally applicable to embodiments that require atrial electrode placement at the anterior atrial wall, such as those embodiments shown in FIGS. 3 and 5.

Figure 8:
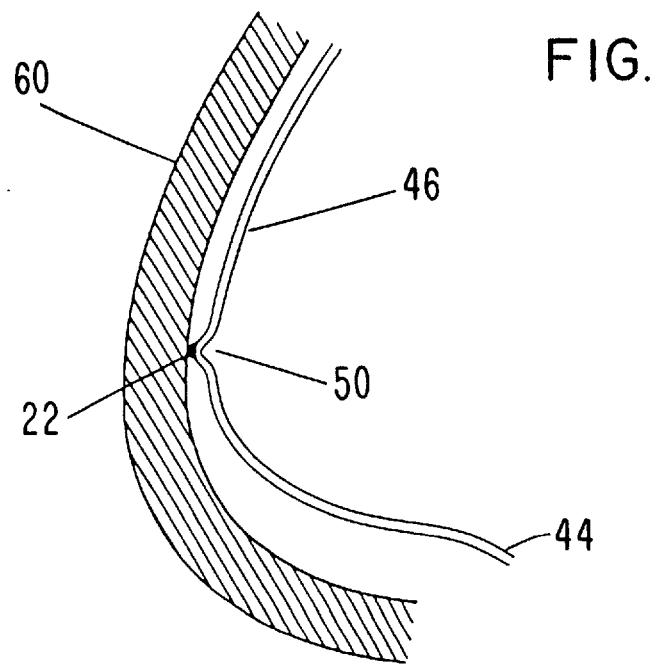
FIG. 8 is a schematic view of a preformed prominence formed in the catheter to ensure proper atrial electrode contact with the atrial wall of the heart.
Figure 9:
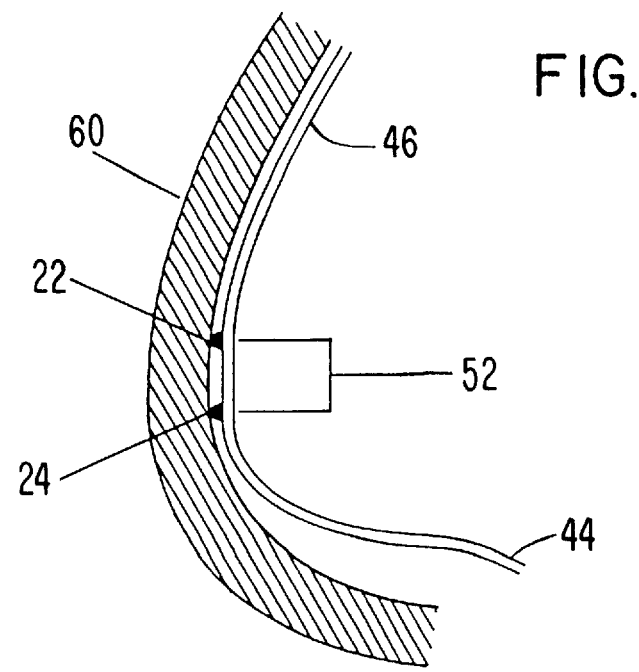
FIG. 9 is a schematic view of a preformed rigid section formed between multiple atrial electrodes to ensure proper atrial electrode contact with the atrial wall of the heart.

In addition to providing a general conformal shape of the catheter along the atrial wall 34 as shown in FIGS. 1–7, it may also be beneficial to preshape a minor projection or prominence 50 in the region of the catheter body 70 that houses the atrial electrodes 22, 24. As shown in FIG. 8, when using a single electrode 22, a minor projection 50 may be preformed into the catheter 70 to enhance proximity of the electrode 22 to the atrial wall 60. The projection 50 may be formed in the catheter body 70 at the electrode site 22 during heat-setting of the elastomer insulation of the catheter 70 as a whole. When using two or more electrodes 22, 24 the structure shown in FIG. 9 may be employed. By either heat-setting or integration of a rigid mechanical structure, a rigid section 52 located between the electrodes 22, 24 provides the advantages of the projection or prominence discussed with respect to FIG. 8, for a two-electrode configuration. This configuration enhances projection of the two tangent points of the catheter body 70 on the atrial wall 60 site of each electrode 22, 24.

In the configurations shown in FIGS. 1–7, holding forces are provided at the wall of the superior vena cava 18 to insure that modest pressure is maintained on the electrodes 22, 24 that are placed lower on the catheter 70 and facing the atrial wall 34 or 36 (i.e., lateral or anterior atrial walls, respectively). In the vicinity at or just above the tricuspid valve 30, a modest bend 72 or multiple bends 74 (as shown in FIG. 2) are preformed to absorb and mitigate forces that tend to displace the conformal atrial section 46 of the catheter 70. The ventricular section 44 of the catheter 70 also requires sufficient pliancy or flexibility and/or stress release bends 74 to prevent excess motion relative to the ventricular electrode 41, to prevent perforation of the ventricular electrode 41 through the ventricular muscle during systole and to provide stable anchoring at the distal end of the catheter 70 to prevent dislodging of the ventricular electrode 41. Fixation of the distal end of the catheter 70 using passive tines 38 and/or active screw mechanisms 40 provides additional insurance against post-implant dislodging of the ventricular electrode 41 and aids in stabilizing of the entire complex for long-term, chronic, dual-chamber pacing.

Selecting the diameter of the catheter 70, particularly in the superior vena cava 18 and against the atrial walls 34, 36, involves consideration of the forces applied to cardiac tissue and the frictional forces operative to mitigate radial and longitudinal motion during cardiac depolarization. The current trend toward use of small diameter catheters may not be necessary for dual-chamber pacing when only one catheter is required, as in the present invention. Larger diameter catheters are useful for dispersing the forces against the cardiac tissue, to allow greater control of the resiliency of various portions of the catheter, and to aid positional stability via the inherently larger frictional forces opposing motion at the various catheter/tissue interfaces or points of contact.

To ease catheter placement, a visual indicator 16 may be disposed on the proximal section 42 of the catheter 70 as shown in FIGS. 1–7. The indicator 16 is used in combination with the straightening stylet 10 during the implant procedure to provide an indication of the angular orientation of the catheter 70 within the heart chamber prior to deployment of the preformed shape upon removal of the stylet 10.

Figure 10:
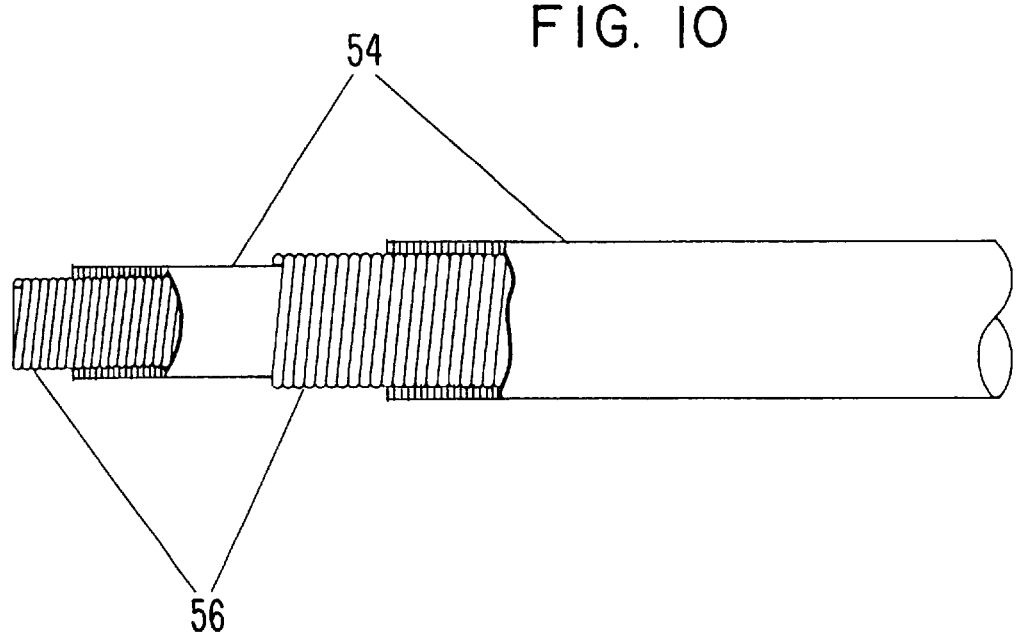
FIG. 10 is a cross-sectional view of the space-wound coaxial coil conductors and insulation which make up the catheter body.
Figure 13:
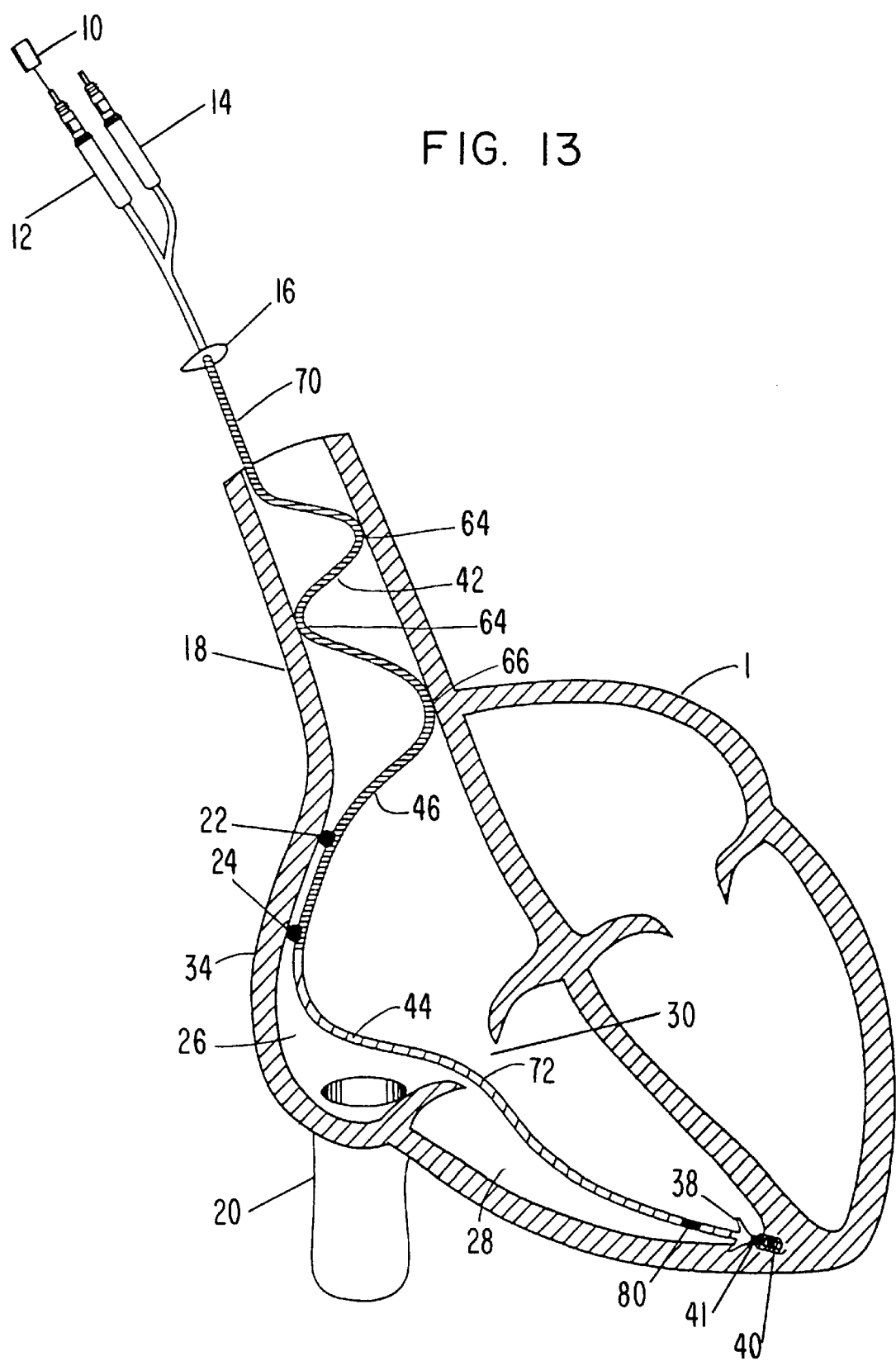
FIG. 13 is a schematic cross-sectional view of another embodiment of the present invention similar to that of FIG. 1, but having additional ventricular electrode.
Figure 14:
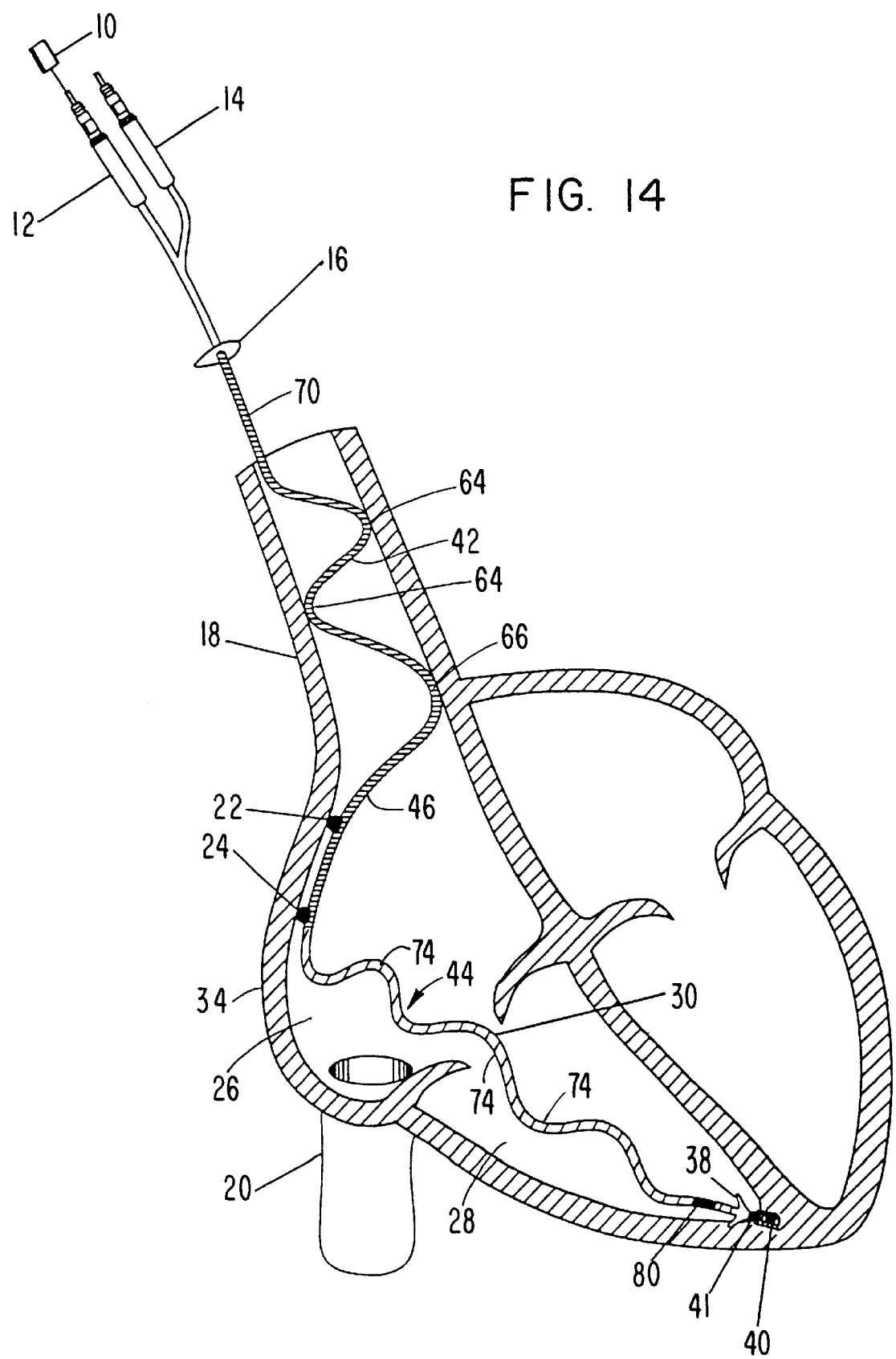
FIG. 14 is a schematic cross-sectional view as shown in FIG. 13, wherein the portion of the catheter between the atrial and ventricular electrodes is also provided with a predetermined amount of additional length and curves.

The design of the elements of the catheter body 70 for forming and maintaining the desired permanent shape is important to provide the attributes discussed above with respect to the present invention. A preferred methodology is to employ insulative materials that are heat-settable to the desired configuration and the provide stable memory for returning the catheter 70 to the desired shape after the stylet 10 has been removed, post implant. In a preferred embodiment of the present invention, two conductors are required for pacing and sensing of both chambers. Referring now to FIG. 10, the two conductors 56 are space wound coaxial coil conductors. A double layer of insulation 54 is also required as shown in FIG. 10. The insulative material is preferably a biocompatible, heat-settable, elastomeric material, such as, for example, heat-settable polyether polyurethane, available under the name BioSpan, from Polymer Technology Corporation. A preferred method of constructing the catheter body is to vertically extrude the polyurethane insulation or other biocompatible elastomer directly onto the individual coils and then slide the smaller coated coil into the larger coated coil prior to heat-setting the assembly. Pre-stressing the conductor coils prior to coating is an optional procedure that aids the memory of shape following final heat-setting of the assembly. Control of the thickness of the insulation material aids in control of the desired pliancy and memory of the assembly. Heat-setting following the assembly of the two coils also ensures cooperative memory of the individual insulative layers. Other methods of manufacturing the catheter may also be employed, including heat-settable extruded elastomer tubing for insulation. Using preformed conductor coils would also aid control of pliancy and memory of the desired shape.

Electrode optimization is also an important consideration in enhancing system performance. Electrode optimization aids contact with cardiac tissue, minimizes cardiac tissue trauma, maximizes detection of cardiac signals and minimizes pacing energy requirements. To this end, the ventricular electrode 41 of the present invention is preferably fixed using passive tines 38 and/or an active fixation screw 40. When using an active fixation screw 40, it is preferred to utilize a guidewire or screwdriver-type mechanism, as described in U.S. Pat. No. 4,217,913 to Dutcher, the disclosure of which is incorporated by reference herein in its entirety. This method allows preforming the entire assembly to achieve the desired memory and pliancy of the catheter. Other methods that require turning of the catheter or an internal section of the catheter are not suitable for use with the present invention, as this has serious drawbacks with respect to maintaining the proper orientation of the preformed catheter in the heart chamber.

There are also many features of electrode configuration that must be considered in employing the catheter configuration of the present invention. Theoretically, electrodes used for both sensing and pacing of cardiac tissue should be relatively small. To pace cardiac tissue, very small electrodes deliver higher current density to excitable cardiac tissue for a given level of absolute current employed, as compared to relatively larger electrodes. Small electrodes also lower the excitation energy thresholds required to stimulate cardiac muscle, thereby minimizing the energy consumption required during pacing. Likewise, very small electrodes are ideally suited for sensing cardiac depolarization, as described in my earlier U.S. Pat. No. 5,127,403, the disclosure of which is incorporated by reference herein in its entirety. The depolarization wavefront dimensions in cardiac tissue are on the order of 1 mm or less, and contacting electrodes of similar size are theoretically ideal. However, there are certain problems attendant with small electrodes because the impedance levels associated with small electrodes are too high to prevent sensing of cross-talk encountered during opposite channel pacing in the wet chronic environment, and/or bridge-loading of signals by way of fluid path leakage currents in the wet chronic environment. Pacing thresholds also elevate chronically, when employing small electrodes due to tissue fibrosis at the electrode site. The fibrosis effectively increases the size of the virtual electrode formed by the combined metallic electrode and the non-excitable fibrous capsule. Because of the technical conflicts noted above with respect to small electrodes, electrode surface areas of smaller than about 4 $mm^2$ have been determined by historical empirical experience to be problematic for permanent pacing electrodes.

Enhancement of detection of atrial depolarization and the pacing function in the atrial chamber also requires consideration of electrode shape. Among these considerations is the desire to enhance the probability of maintaining contact with the excitable cardiac tissue for pacing, and to optimize the shape to enhance detection of the propagating depolarization event. In addition to forming a projection or prominence in the preformed catheter as described above with respect to FIGS. 8 and 9, in order to maximize the probability of atrial wall contact, the electrode should protrude beyond the mean diameter of the catheter such that the electrode presses into cardiac tissue. This feature is illustrated in FIGS. 11 and 12. Another consideration is the variable terrain of the pectinate muscles in some areas of the interior wall of the atrium. This non-uniform surface containing many peaks and valleys dictates either using multiple electrodes or one electrode designed with dimensions and shape factors that take into account the irregularities of the inner wall surface of the atrium. The pectinate muscle typically has valleys having depths in the range of 2 to 3 mm and widths in the range of 2 to 3 mm.

As shown in FIGS. 11 and 12, the exposed metal of the electrodes 22 should not completely encircle the catheter 70 because the back side, i.e., the side facing away from the inner wall 58 of the atrial wall 60, would waste the pacing current delivered into the blood pool. Furthermore, back-side exposure of the electrode 22 to the reduced field strength depolarization signal in the blood pool compared to the strength at the contact point averages down the resultant amplitude of the signal as observed only on the side of the electrode 22 facing the cardiac tissue 58. Additionally, because of the unknown exact angle of lay of the catheter 70 against the cardiac tissue 58, it is heuristically prudent to have the electrode 22 surround a portion of the catheter 70, but shaped so as not to substantially increase the overall catheter diameter any greater than the protrusion dimension of the electrode 22 in the direction of the atrial wall as shown in FIGS. 11 and 12. In FIGS. 11 and 12, the back-side of the electrode is formed into a ring that fully surrounds the outer conducting coil and is crimped in a place along the edges 64 during assembly prior to application of a final coat or sleeve 54 over the catheter 70 that insulates both the back-side facing away from the cardiac tissue 58 and the crimp area 64. The most important consideration in mechanical electrode attachment is to provide assurance against back-side exposure of the electrode to the blood pool and adequate mechanical fixation of the electrode 22 to the catheter body 70 to prevent accidental loosening and escape from the catheter body.

Referring now to FIGS. 1–7, two electrodes 22, 24 are shown deployed in the atrial chamber 26. Clinical experience may provide the statistical evidence to determine whether one or two electrodes are optimum. Both atrial electrodes 22, 24 shown in FIGS. 1–7 are mechanically and electrically connected to the outer conductor coil used to transport atrial pacing signals to the electrode from the pacemaker and atrial signals from the electrode to the pacemaker. It is known to those in the art that each electrode's performance for both pacing and sensing is degraded by the other electrically parallel, but spatially separated, electrodes. The current density for pacing at each electrode site is diminished by a factor of two, given a constant current source and equal surface areas, since current is equally distributed to both electrodes. Degradation of sensing also occurs with use of an electrically parallel electrode pair. This degradation occurs because the atrial depolarization wave front passes each electrode at different times and loading by the electrode at the inactive site attenuates the signals present at the alternate electrode site of depolarization activity. The atrial signal to far-field ventricular signal ratio is degraded if the electrode separation is such that both electrodes simultaneously observe like amplitude and phase ventricular signals. General attenuation of the atrial signals can be accommodated by using increased sensitivities in the atrial sensing electronics. Atrial to ventricular signal ratios can also be improved using atrial sensing filters tuned to the spectral content of atrial signals as developed on small surface area contact electrodes or electrodes proximate to cardiac tissue. Use of one electrode would, of course, be theoretically ideal with respect to electrical pacing/sensing requirements, but these pacing/sensing compromises using two electrodes would aid in the probability of achieving the desired tissue contact or close proximity of one or the other electrode to the atrial wall. However, with proper dimensioning of a single electrode to bridge the valleys of the pectinate muscles combined with the optimum preformed catheter body shape to serve as the platform for the electrode, the single atrial electrode may indeed provide the most elegant configuration for single-catheter, dual-chamber pacing systems.

Turning now to FIGS. 13–19, the embodiments shown therein substantially parallel those shown in FIGS. 1–7, with an additional electrode 80 disposed in a ventricular portion of the catheter. The additional ventricular electrode 38 may be a ring electrode. Ring electrodes and their characteristics are well-known in the art and the particular size and positioning of the electrode will be determinable by one of ordinary skill in the art in view of the present disclosure.

Pacemaker systems are generally defined as being unipolar or bipolar. As such, both single chamber pacing with one lead or dual chamber pacing with two leads can be configured to be either unipolar or bipolar. Unipolar systems use the pacemaker case as one of the electrical poles that, in combination with the pacing electrode on a catheter, forms a complete electrical circuit from the pacing system through the body tissue and return. In bipolar systems, on the other hand, the return electrode is housed on the lead as a second electrode to serve as the return electrical path instead of using the metallic pacemaker housing.

Recently, pacemaker systems have been developed but provide mixed unipolar or bipolar functionality. Additionally, such systems may also be reversible between which of the two poles serves as the "return" path. Systems having this reversible feature are called polarity-programmable.

In bipolar systems, the negative pole (i.e., negative pulse polarity) supplies more effective stimulation relative to the ease of inducing depolarization of cardiac muscle cells as compared to using the positive pole. This factor is important in enhancing the effectiveness and reliability of chronic atrial pacing where electrodes may not maintain positional stability beat by beat, as discussed above.

Several embodiments of the invention beyond those of the shaping methods described above involve various uses of the electrodes disposed on the pacing catheter. Having two electrodes in each chamber housed on a common catheter can provide both bipolar sensing and pacing in each chamber.

In a preferred embodiment, a full bipolar version of the single catheter includes four conductors 56 (see FIG. 20) for bipolar sensing and pacing in both heart chambers 26, 28. Four layers of insulation 54 are also required for a full dual bipolar system and three conductors and layers of insulation (not shown) are required for mixed systems that are unipolar in the ventricular chamber 28 and bipolar in the atrium 26. As set forth above, a preferred method of constructing the catheter body 70 is to vertically extrude polyether polyurethane insulation or other biocompatible elastomer directly on to each of the individual coils 56 and then slide the smaller coils into the longer coated coils prior to heat-setting the catheter in the desired shape and configuration.

Figure 20:
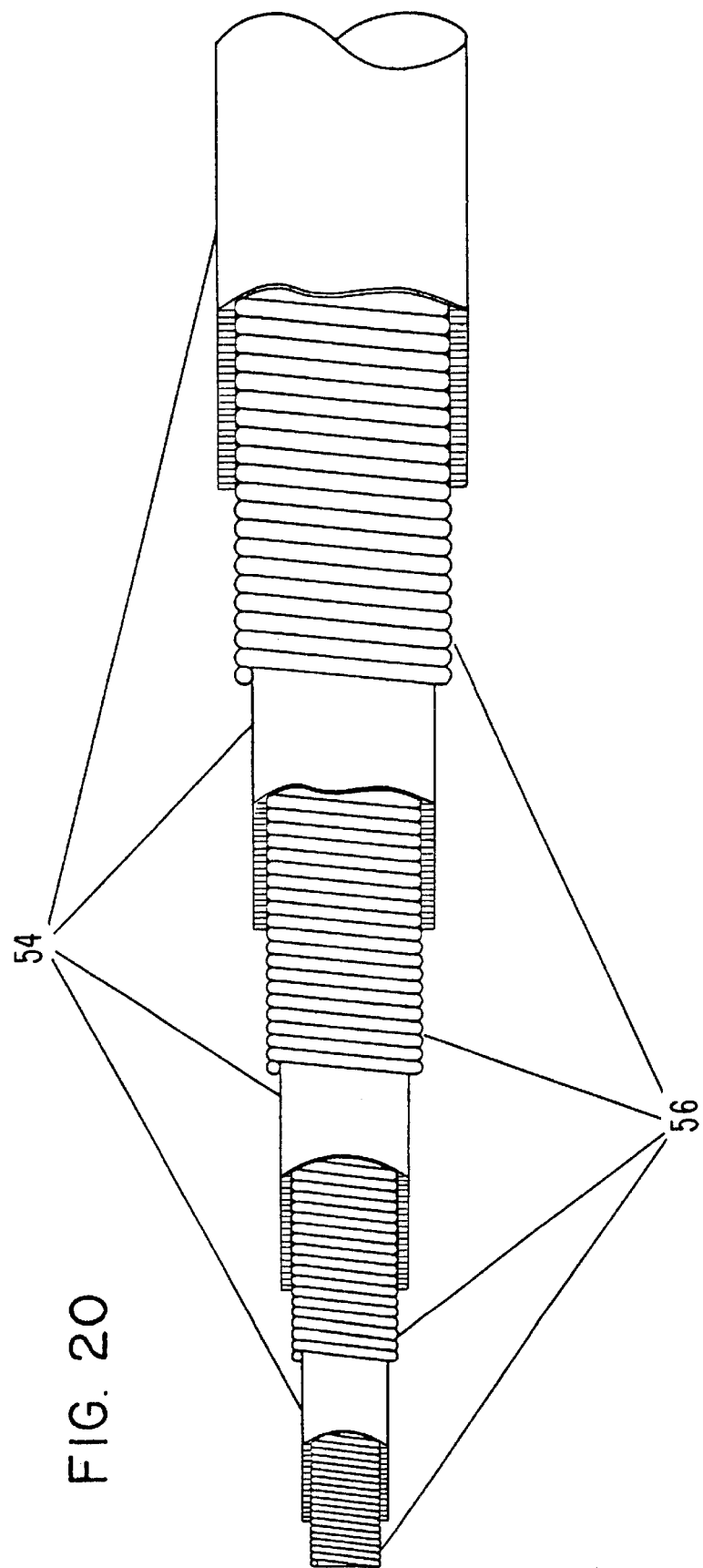
FIG. 20 is a cross-sectional view as shown in FIG. 10, but having four space-wound coaxial coil conductors and insulation which makes up the catheter body.

In addition to configurations in which bipolar performance is desired in both chambers of the heart, as shown in FIGS. 13–19, wherein two electrodes are required in each chamber, thus requiring a catheter having four conductors as shown in FIG. 20, various combinations of bipolar and unipolar configurations are contemplated. For example, in another preferred embodiment, thinner conductors would be used to pace and sense on one unipolar electrode in the ventricle, pace unipolar parallel on a pair of electrodes in the atrium and sense bipolar on the same pair of atrial electrodes. Switching between parallel unipolar atrial pacing and bipolar atrial sensing may be accomplished in the pacemaker electronics 102. Unipolar pacing and sensing in the ventricle in combination with parallel unipolar pacing in the atrium and differential bipolar sensing in the atrium may provide the best and most reliable system for delivering dual chamber pacing therapy. It should be noted that for atrial pacing that electrodes should be spaced in the range of 0.5 to 1 cm rather than 1 to 3 mm. Sensing is known to be reliable in this range for floating electrodes and even more reliable in this range for with close proximity to the atrial wall. The pacing function is of more critical concern and dimensioning should favor optimizing for that function.

Figure 15:
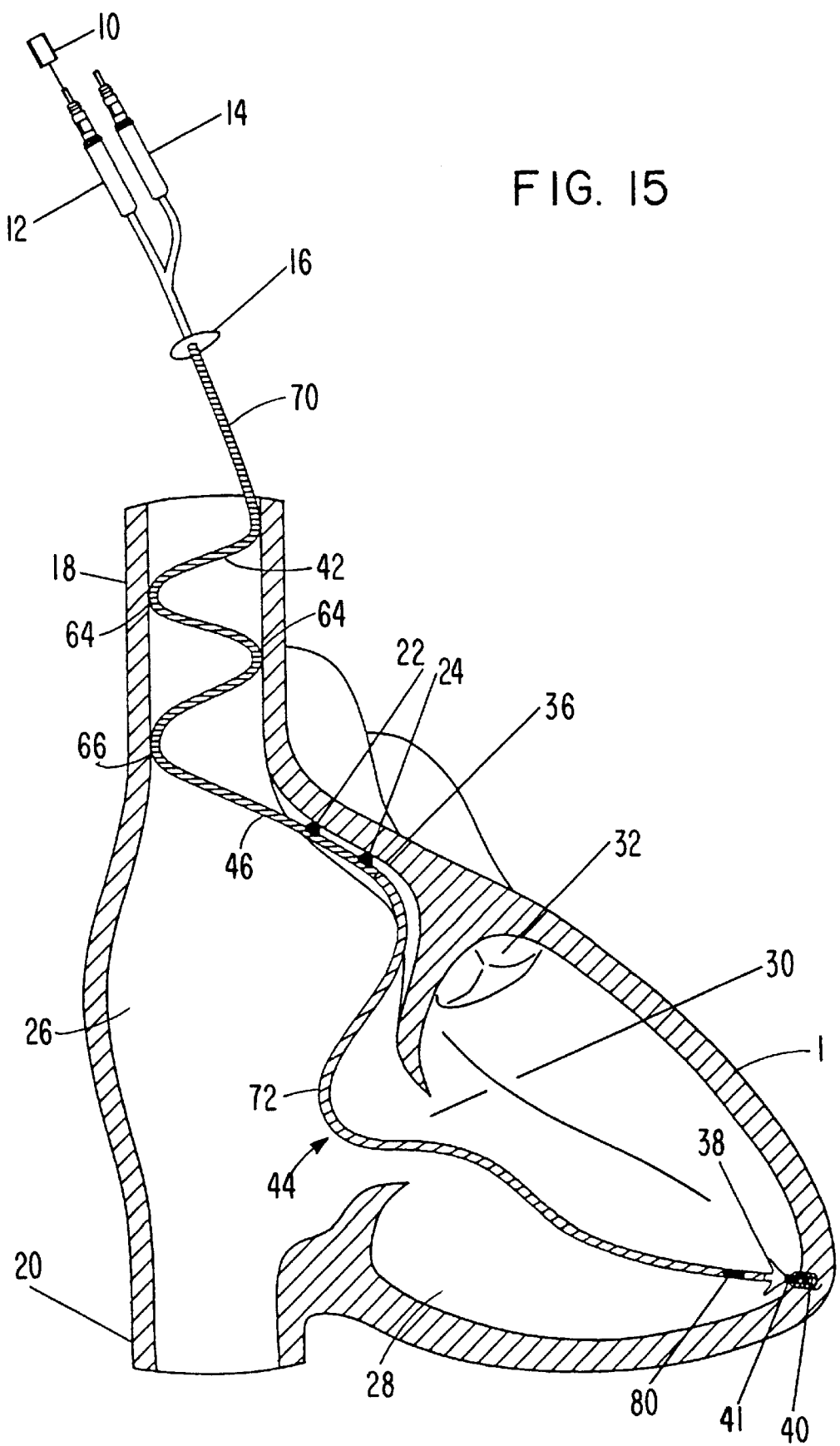
FIG. 15 is a schematic cross-sectional view as shown in FIGS. 13 and 14, but with the atrial electrodes being disposed on the anterior wall of the atrium.
Figure 16:
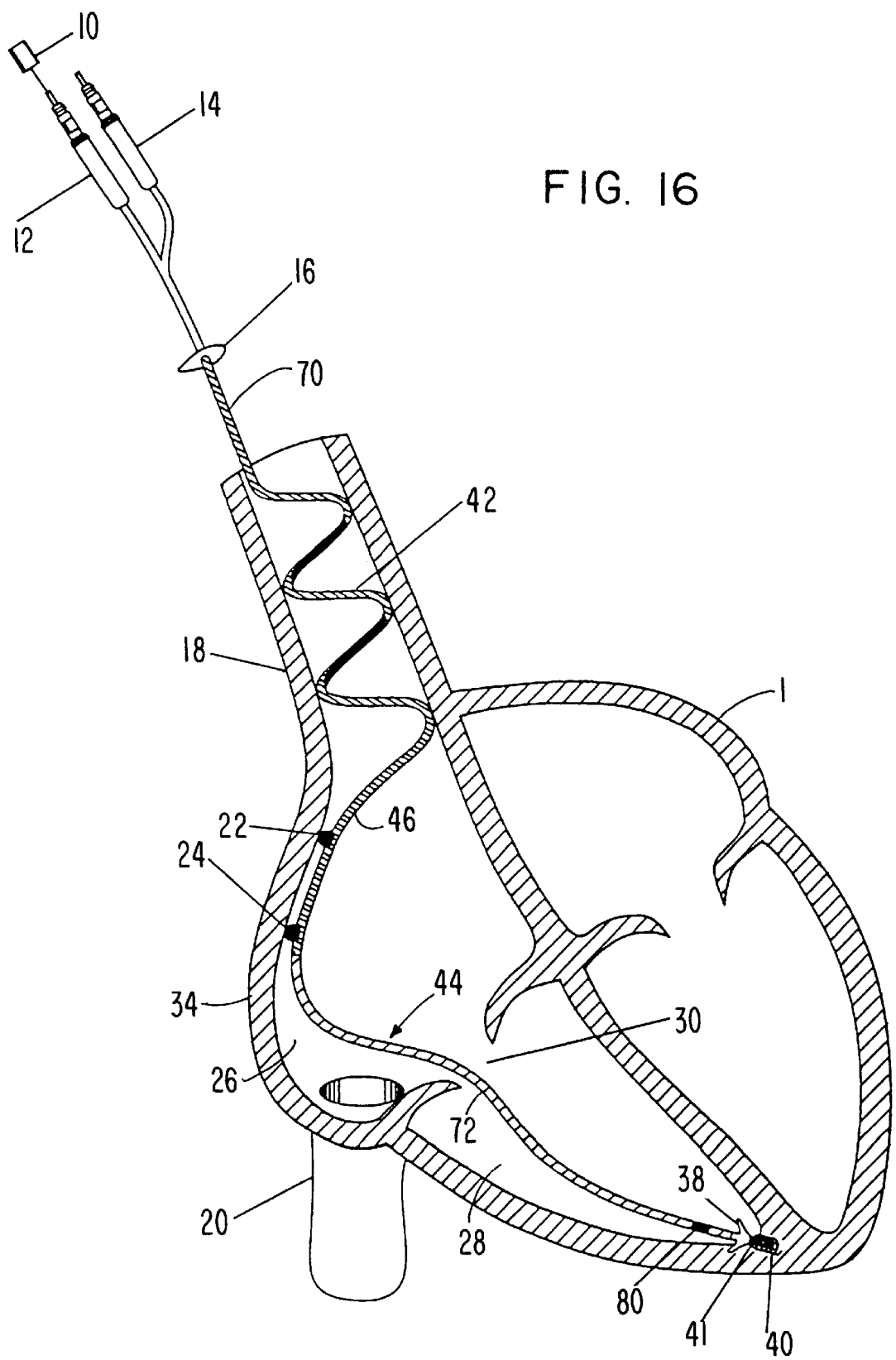
FIG. 16 is a schematic cross-sectional view as shown in FIG. 4, but having an additional ventricular electrode.
Figure 17:
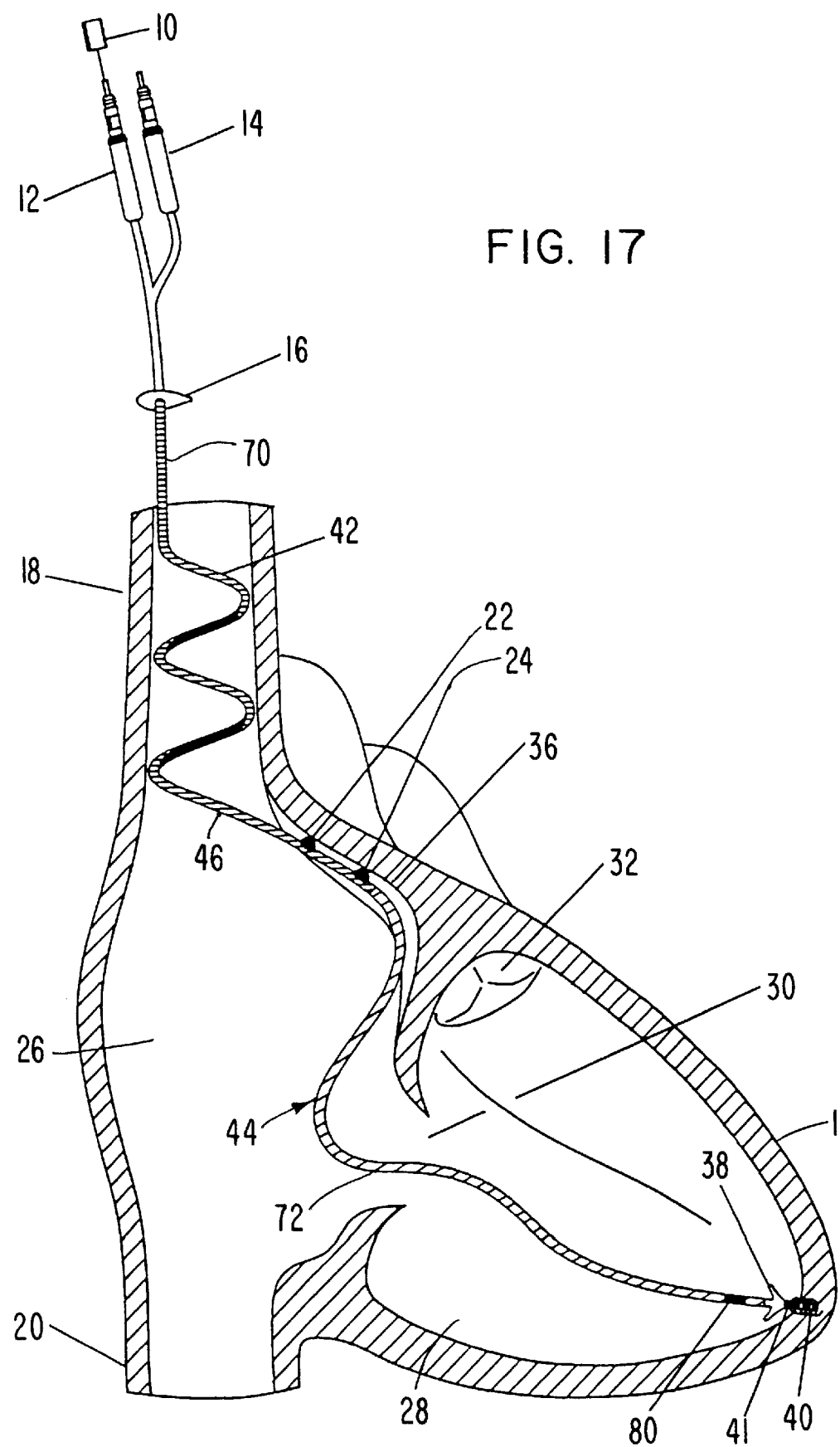
FIG. 17 is a schematic cross-sectional view of the embodiment of the present invention shown in FIG. 11, but with the atrial electrodes being disposed on the anterior wall of the atrium.
Figure 18:
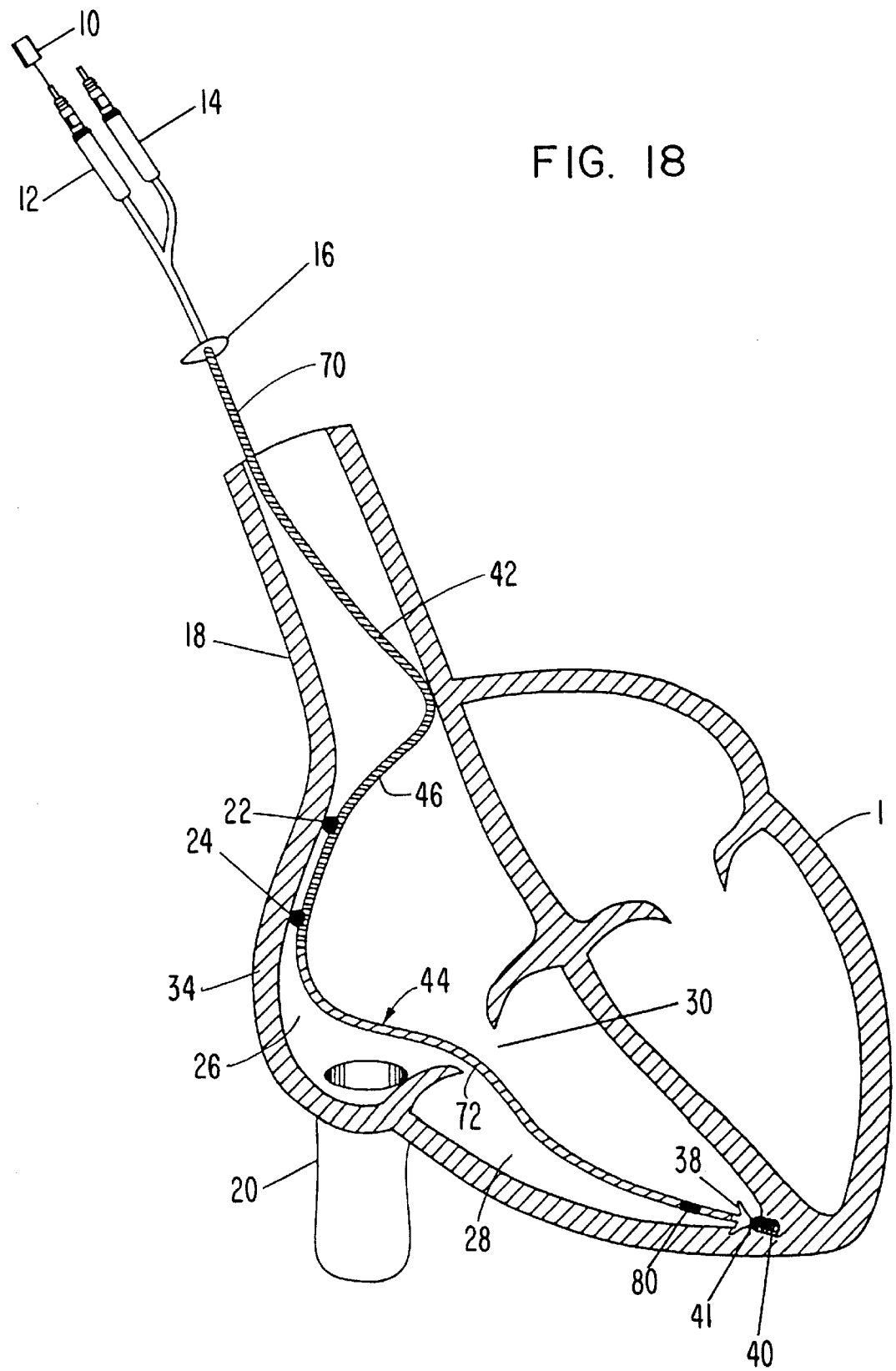
FIG. 18 is a schematic cross-sectional view as shown in FIG. 6, but having an additional ventricular electrode.
Figure 19:
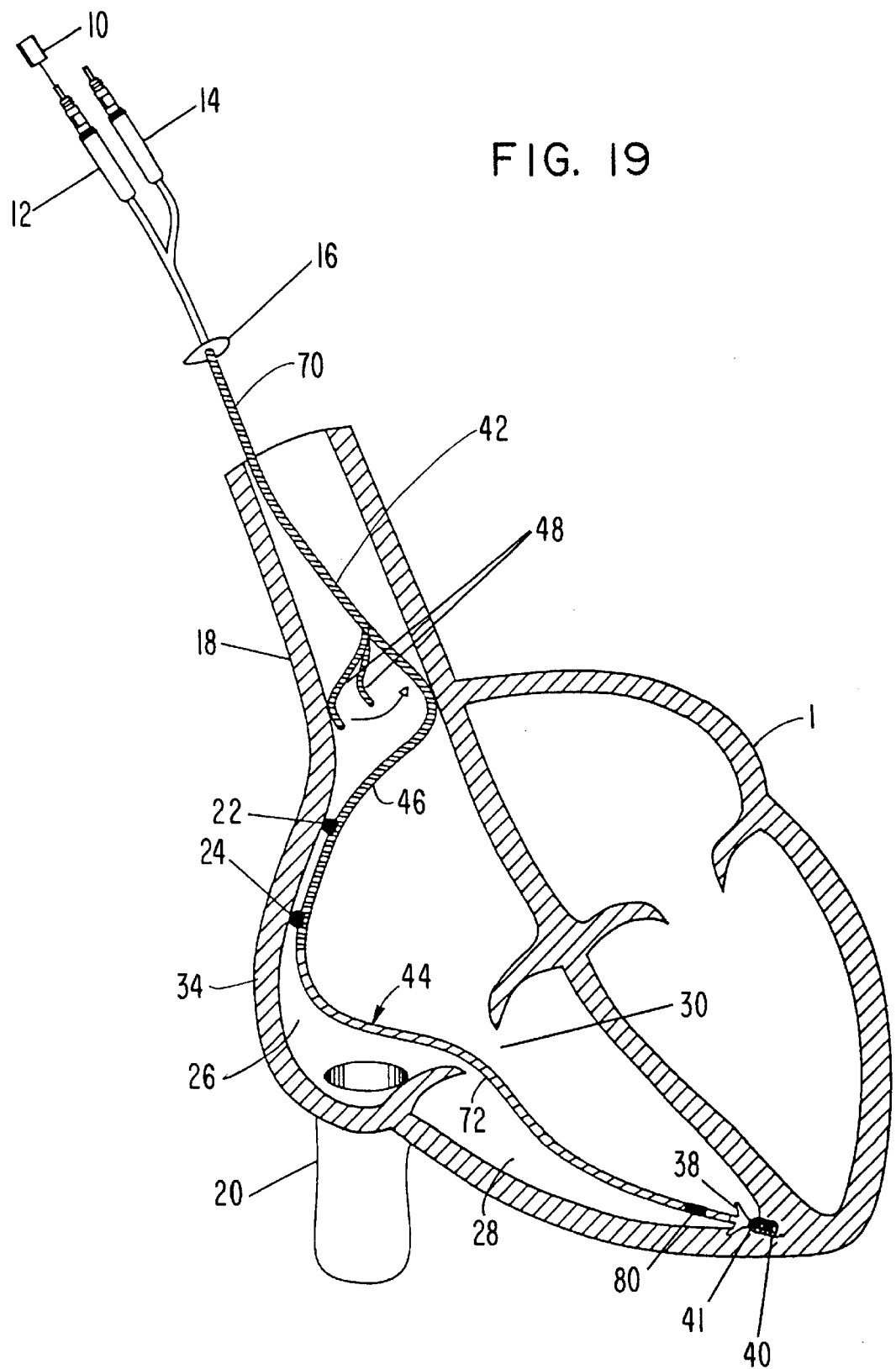
FIG. 19 is a schematic cross-sectional view as shown in FIG. 7, but having an additional ventricular electrode.

With regard to the most preferred deployment of atrial electrodes on the interior of the atrial wall, there are some critical considerations. If sensing and not pacing is the desired function of the electrodes, the location of electrodes is less critical. If, however, both pacing and sensing is the desired function, the anterior wall 36 provides the best location for the electrodes, as shown in FIGS. 3, 5 and 15, for avoidance of phrenic nerve stimulation, as the best location to trap the catheter against angular rotation and the preferred location to prevent electrode suspension caused, for example, by bridging of the catheter across the cavity of the atrial appendage with the catheter located medial to the anterior wall 36.

In accordance with another aspect of the instant invention, improved stability of the pacing function can be achieved when using any suitable pacing catheter having at least two electrodes by using bipolar sensing in conjunction with parallel unipolar pacing. Switching between bipolar sensing and parallel unipolar pacing can be accomplished by providing switchable electronics 102 in the pacemaker 100 associated with the catheter. The instant inventor has found that using switchable electronics 102 to switch between bipolar sensing and parallel unipolar pacing improves the stability of the pacing, at least in part, by reducing the possibility of degraded functioning due to electrode suspension caused by bridging of the catheter along the interior wall of the heart. It is noted that the feature of providing switchable electronics to achieve bipolar sensing and parallel unipolar pacing is not limited to use in connection with the particular catheter disclosed herein, but may be used with any known suitable pacing catheter to increase the operational stability thereof in one or more chambers of the heart.

In accordance with a further aspect of the instant invention, if it is desired to use atrial bipolar stimulation rather than unipolar parallel stimulation, the beat by beat uncertainty of which electrode is closest to active tissue can be accommodated by delivery of a bipolar stimulus of one polarity on the pair of electrodes followed immediately by a reverse polarity stimulus. By use of this double polarity stimulus, it is assured that the electrode with the best instantaneous proximity to active tissue will serve as the more efficient cathodal (negative) stimulation function. To reiterate, stimulation reliability can be improved by use of two electrodes in a parallel unipolar configuration or the two electrodes can be employed bipolar provided both polarities of stimulus voltage are applied sequentially to the electrode pair to assure cathodal usage of the electrode in closest proximity to active tissue. The sequential alternate stimulation pulses can be generated by suitable electronics 102 in the pacemaker 100 associated with the catheter.

While this invention has been described in conjunction with specific embodiments thereof, it is evident that many alternatives, modifications and variations will be apparent to those skilled in the art. Accordingly, the preferred embodiments of the invention, as set forth herein, are intended to be illustrative, not limiting. Various changes may be made without departing from the true spirit and full scope of the invention, as defined in the following claims.

I claim:

1. A single catheter for pacing and sensing atrial and ventricular chambers of the heart, said catheter comprising:
   a first catheter section having a preformed shape for positioning in a superior vena cava, said preformed shape providing stability for said catheter;
   a second catheter section below the first catheter section for positioning in said atrial chamber, said second catheter section having at least one atrial electrode disposed thereon, said second catheter section being preformed to generally conform to an inner wall of the atrium and to be held in proximity to said inner wall by said first catheter section when said catheter is positioned in said heart;
   a third catheter section disposed between said at least one atrial electrode and a distal end of said catheter for positioning in said ventricular chamber of the heart, wherein said first and second catheter sections each have a given pliancy and said third catheter section has a pliancy greater than said given pliancy of said first and second catheter sections to provide stress release to said catheter when positioned in said heart; and
   a first ventricular electrode disposed at the distal end of the catheter for use in pacing and sensing of the ventricular chamber.

2. The catheter of claim 1, wherein said catheter includes a catheter body comprising two insulated space-wound coaxial coils, said coils providing electrical conduction for pacing and sensing the atrial and ventricular chambers of the heart.

3. The catheter of claim 2, wherein said catheter body is made of a material comprising a biocompatible heat-settable material.

4. The catheter of claim 3, wherein said biocompatible heat-settable material comprises polyether polyurethane.

5. The catheter of claim 1, further comprising an indicator disposed at a proximal end thereof above the first catheter section, said indicator indicating an angular position of said catheter during implant.

6. The catheter of claim 1, wherein said at least one atrial electrode is positioned on said catheter to face the atrial wall when said catheter is positioned in said heart.

7. The catheter of claim 6, wherein said catheter includes a projection formed therein at a location of said at least one atrial electrode.

8. The catheter of claim 1, including means for receiving a straightening stylet to facilitate insertion of said catheter into the venous system during implant of said catheter in said heart.

9. The catheter of claim 8, wherein said straightening stylet comprises a plurality of longitudinal markers that appear sequentially at a proximal end of said catheter during removal of the stylet to indicate advance of the catheter into the venous system.

10. The catheter of claim 1, further comprising a passive fixation device disposed at the distal end thereof for securing a position of said first ventricular electrode against the ventricle when positioned in said heart.

11. The catheter of claim 10, wherein the passive fixation device comprises passive fixation tines.

12. The catheter of claim 10, further comprising an active fixation device having means for enabling said active fixation device to be controlled by a stylet inserted in said catheter, said active fixation device being disposed at the distal end of said catheter and cooperating with said passive fixation device to secure the position of said first ventricular electrode against the ventricle.

13. The catheter of claim 12, wherein said active fixation device comprises an active fixation screw and said passive fixation device comprises passive fixation tines.

14. The catheter of claim 1, further comprising an active fixation device having means for enabling said active fixation device to be controlled by a stylet inserted in said catheter, said active fixation device being disposed at the distal end of said catheter for securing a position of said first ventricular electrode against the ventricle.

15. The catheter of claim 14, wherein said active fixation device comprises an active fixation screw.

16. The catheter of claim 1, wherein said third catheter section includes a preshaped bent portion located between said at least one atrial electrode and a point where said third catheter section passes through a tricuspid valve when said catheter is positioned in said heart, said preshaped bent portion absorbing and mitigating heart motion forces on said second catheter section when said catheter is positioned in said heart.

17. The catheter of claim 1, wherein said at least one atrial electrode comprises at least two atrial electrodes for sensing and stimulating the atrial chamber of the heart.

18. The catheter of claim 17, wherein said at least two atrial electrodes are positioned on said catheter to face said inner wall of the atrium when said catheter is positioned in said heart.

19. The catheter of claim 18, wherein said at least two atrial electrodes protrude from said catheter on a side of the catheter for facing the inner wall of the atrium when said catheter is positioned in said heart.

20. The catheter of claim 19, wherein said electrodes have surface areas in the range of 3 to 15 mm².

21. The catheter of claim 19, wherein said electrodes have a length in a direction parallel to a longitudinal axis of the catheter body in the range of 1 to 6 mm.

22. The catheter of claim 18, wherein said catheter includes a rigid section disposed between said at least two atrial electrodes for projecting said at least two atrial electrodes in an outward direction.

23. The catheter of claim 18, wherein said electrodes have surface areas in the range of 3 to 15 mm².

24. The catheter of claim 18, wherein said electrodes have a length in a direction parallel to a longitudinal axis of the catheter body in the range of 1 to 6 mm.

25. The catheter of claim 17, wherein said at least two electrodes surround a circumference of said catheter.

26. The catheter of claim 25, wherein said at least two atrial electrodes protrude from said catheter in an area designed to face the inner wall of the atrium when said catheter is positioned in said heart.

27. The catheter of claim 26, wherein said electrodes have surface areas in the range of 3 to 15 mm².

28. The catheter of claim 26, wherein said electrodes have a length in a direction parallel to a longitudinal axis of the catheter body in the range of 1 to 6 mm.

29. The catheter of claim 25, wherein said at least two atrial electrodes protrude from said catheter over an entire circumference of said catheter.

30. The catheter of claim 29, wherein said electrodes have surface areas in the range of 3 to 15 mm².

31. The catheter of claim 29, wherein said electrodes have a length in a direction parallel to a longitudinal axis of the catheter body in the range of 1 to 6 mm.

32. The catheter of claim 25, wherein said electrodes have surface areas in the range of 3 to 15 mm².

33. The catheter of claim 25, wherein said electrodes have a length in a direction parallel to a longitudinal axis of the catheter body in the range of 1 to 6 mm.

34. The catheter of claim 1, wherein said first catheter section comprises a plurality of preformed curved sections for positioning in the superior vena cava.

35. The catheter of claim 1, wherein said first catheter section comprises a plurality of preformed spiral loops for positioning in the superior vena cava.

36. The catheter of claim 1, wherein said first catheter section comprises a single preformed lobe section for positioning in the superior vena cava and a preformed lever arm section disposed above said lobe section, said lever arm section providing stabilization for said catheter and said lobe section acting as a fulcrum.

37. The catheter of claim 36, wherein said preformed lever arm section is disposed above a lobe point where said lobe section is designed to contact the superior vena cava when positioned therein, said lever arm section providing stabilization for said second catheter section, said lobe section providing a lever fulcrum for said second catheter section and said lobe point providing a lever arm restraint with a wall of the superior vena cava when positioned therein, wherein said preformed lobe section is positioned such that said lobe section is located adjacent an exit of the superior vena cava into the atrium when said catheter is positioned therein.

38. The catheter of claim 1, wherein said first catheter section includes at least one splayed projection arm extending from said first catheter section in a portion of said first catheter section for positioning inside the superior vena cava, said at least one splayed projection arm stabilizing the second section against the inner wall of the atrium when said catheter is positioned in said heart.

39. The catheter of claim 38, comprising at least two of said splayed projection arms extending from the first catheter section, said at least two splayed projection arms being radially positioned about the catheter.

40. The catheter of claim 39, wherein said at least two splayed projection arms are positioned to angularly extend approximately 120° from each other and are also positioned to angularly extend approximately 120° from the catheter.

41. The catheter of claim 39, wherein said splayed projection arms are foldable against the catheter and are held in a folded position by a biocompatible dissolvable material during implant, said projection arms extending from said catheter when said dissolvable material is dissolved.

42. The catheter of claim 41, wherein said splayed projection arms are oriented to face distally toward the exit of the superior vena cava when said catheter is positioned in said heart to facilitate removal of the catheter from said heart.

43. The catheter of claim 39, wherein said splayed projection arms are foldable against the catheter and are held in a folded position by a string knot retainer during implant, said projection arms extending from said catheter when the string knot retainer is released by extension of a string of the retainer.

44. The catheter of claim 43, wherein said splayed projection arms are oriented to face distally toward the exit of the superior vena cava when said catheter is positioned in said heart to facilitate removal of the catheter from said heart.

45. The catheter of claim 39, wherein said splayed projection arms are foldable against the catheter and are held in a foldable position by a biocompatible dissolvable material during implant, said projection arms extending from said catheter when the biocompatible dissolvable material dissolves by contact with the blood pool.

46. The catheter of claim 45, wherein the splayed projection arms are oriented to face distally toward the exit of the superior vena cava when said catheter is positioned in said heart to facilitate removal of the catheter from said heart.

47. The catheter of claim 1, wherein said second catheter section includes two atrial electrodes and said catheter includes a catheter body comprising three insulated spacewound coaxial coils connected with said two atrial electrodes and said first ventricular electrode, respectively, said coils providing electrical conduction for pacing and sensing the atrial and ventricular chambers of the heart.

48. The catheter of claim 47, further comprising a second ventricular electrode disposed proximally of said first ventricular electrode and in a ventricular chamber of the heart.

49. The catheter of claim 48, wherein said second ventricular electrode is a ring electrode.

50. The catheter of claim 47, wherein two of the three spaced-wound coaxial coils terminate in the atrial chamber of the heart for connection with said two atrial electrodes, and a third space-wound coaxial coil terminates in the ventricle for connection with said ventricular electrode.

51. The catheter of claim 50, wherein said catheter is connected to means which enables said two atrial electrodes to be electronically switchable to sense bipolar and pace unipolar parallel.

52. The catheter of claim 51, wherein at least one of said atrial electrodes functions as the atrial pacing electrode.

53. The catheter of claim 1, wherein said second catheter section includes two atrial electrodes and said third catheter section includes a second ventricular electrode, and further wherein said catheter includes a catheter body comprising four insulated space-wound coaxial coils connected to said two atrial electrodes and said first and second ventricular electrodes, respectively, said coils providing electrical conduction for pacing and sensing the atrial and ventricular chambers of the heart.

54. The catheter of claim 53, wherein said second ventricular electrode is a ring electrode.

55. The catheter of claim 53, wherein two of the four space-wound coaxial coils terminate in the atrial chamber of the heart for connection with said two atrial electrodes, and another two of the four spaced-wound coaxial coils terminate in the ventricle for connection with said first ventricular electrode and said second ventricular electrode.

* * * * *